United States Patent [19]

Kimura

[11] 4,156,777
[45] May 29, 1979

[54] PROCESS FOR PRODUCING GLUCOPYRANOSE-NITROSOUREA COMPOUNDS AND NOVEL COMPOUNDS INCLUDED THEREIN

[75] Inventor: Goro Kimura, Kamakura, Japan

[73] Assignee: Tokyo Tanabe Company, Limited, Japan

[21] Appl. No.: 872,384

[22] Filed: Jan. 26, 1978

[30] Foreign Application Priority Data

Feb. 3, 1977 [JP] Japan ................... 52-10220

[51] Int. Cl.$^2$ ............... C07H 19/00; C07H 21/00; A61K 31/70
[52] U.S. Cl. ........................... 536/22; 536/53; 536/4; 536/18; 424/180
[58] Field of Search ................ 536/53, 22, 18, 4

[56] References Cited

U.S. PATENT DOCUMENTS 4,057,684  11/1977  Kimura et al. ................ 536/4
4,086,415  4/1978  Suami et al. ................ 536/53

Primary Examiner—Johnnie R. Brown
Assistant Examiner—Blondel Hazel
Attorney, Agent, or Firm—McGlew and Tuttle

[57] ABSTRACT

Glucopyranose-nitrosourea compounds having lower alkyl group and/or 2-chloroethyl group as substituent(s), are produced at high yield by reacting amino-glucopyranose compounds having lower alkoxy group and/or amino group(s) (or an acid-added amino group) as substituent(s), with o-nitro- or o-cyano-phenyl N-substituted-N-nitrosocarbamate compounds having lower alkyl group or 2-chloroethyl group as substituent. 1-(Lower alkyl or 2-chloroethyl)-3-(D-glucopyranos-6-yl)-1-nitrosourea compounds included within the scope of the nitrosourea compounds are novel. The nitrosourea compounds produced by this invention all show antitumor activity, among which the novel compounds exhibit excellent physical and pharmacological properties.

22 Claims, No Drawings

PROCESS FOR PRODUCING GLUCOPYRANOSE-NITROSOUREA COMPOUNDS AND NOVEL COMPOUNDS INCLUDED THEREIN

BACKGROUND OF THE INVENTION

1. Field of the Invention

This invention is concerned with improvements in or relating to glucopyranose-nitrosourea compounds.

In particular, the invention relates to a process for the production of glucopyranose-nitrosourea compounds which have antitumor activity. The compounds produced by the process of the invention have the following general formula:

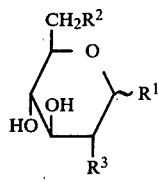   [I]

in which $R^1$ represents one member selected from the group consisting of hydroxy group, alkoxy group having from 1 to 4 carbon atoms and $N_1$-substituted-1-nitrosourea group of formula

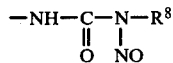

(wherein $R^8$ represents an alkyl group having from 1 to 4 carbon atoms or a 2-chloroethyl group); and $R^2$ and $R^3$, which may be the same or different, each represents a hydroxy group or an $N_1$-substituted-1-nitrosourea group of formula

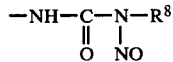

(wherein $R^8$ is as defined above); with the proviso that $R^1$, $R^2$ and $R^3$ are not all the same.

Certain compounds of the general formula I are novel and constitute a further feature of the invention. The novel compounds are characterised by the presence of an $N_1$-substituted-1-nitrosourea group (as defined above) as substituent at the 6-position carbon of D-glucopyranose skeleton in formula I and have the following general formula:

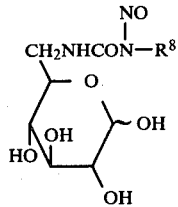   [II]

in which $R^8$ is as defined above.

2. The Prior Art

Various glucopyranose-nitrosourea compounds having antitumor activity have hitherto been disclosed, of which the following compounds have especially been studied in detail:

streptozotocin (hereinafter referred to as "SZ");

alkyl streptozotocin (hereinafter referred to as "alkyl SZ");

1-(2-chloroethyl)-3-(D-glucopyranos-2-yl)-1-nitrosourea (hereinafter referred to as "DCNU");

1-(2-chloroethyl)-3-($\beta$-D-glucopyranosyl)-1-nitrosourea (hereinafter referred to as "GANU");

1-(2-chloroethyl)-3-(methyl $\alpha$-D-glucopyranos-2-yl)-1-nitrosourea (hereinafter referred to as "2MC$\alpha$G");

1-(2-chloroethyl)-3-(methyl $\alpha$-D-glucopyranos-6-yl)-1-nitrosourea (hereinafter referred to as "6MC$\alpha$G"); and 3,3'-(methyl $\alpha$-D-glucopyranos-2,6-di-yl)-bis[1-(2-chloroethyl)-1-nitrosourea] (hereinafter referred to as "WMC$\alpha$G").

The above-mentioned known glucopyranose-nitrosourea compounds have generally been produced by nitrosating glucopyranose-urea compounds of the following general formula, using nitrite or nitrogen trioxide under acidic conditions:

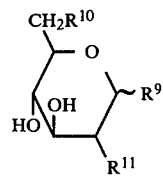   [III]

in which $R^9$ represents one member selected from the group consisting of hydroxy group, alkoxy group having from 1 to 4 carbon atoms and $N_1$-substituted ureido group of formula

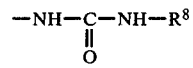

(wherein $R^8$ is as hereinbefore defined); and $R^{10}$ and $R^{11}$, which may be the same or different, each represents a hydroxy group or an $N_1$-substituted ureido group (as defined above); with the proviso that $R^9$, $R^{10}$ and $R^{11}$ are not all the same. Compounds of formula III include, for example, 1-(2-chloroethyl)-3-(alkyl D-glucopyranos-6-yl)urea, 1-(2-chloroethyl)-3-($\beta$-D-glucopyranosyl)urea, 1-(2-chloroethyl)-3-(D-glucopyranos-2-yl)urea, 1-(2-chloroethyl)-3-(alkyl D-glucopyranos-2-yl)urea and 3,3'-(alkyl D-glucopyranos-2,6-di-yl)-bis-[1-(2-chloroethyl)urea]. [cf. Journal of the American Chemical Society, 89 (1967), 4808; Journal of Organic Chemistry, 35 (1970), 245; The Journal of Antibiotics, 25 (1972), 377; Journal of Medicinal Chemistry, 17 (1974), 392; ibid., 19 (1976), 918; ibid., 18 (1975), 104; Organic Preparations and Procedures Int., 6 (1974), 259; Bulletin of the Chemical Society of Japan, 48 (1975), 3763; Eur. J. Med. Chem.-Chimica Therapeutica, 11 (1976), 183; German Pat. Offenlegungsschrift No. 2,530,416; Dutch Pat. Offenlegungsschrift No. 7,507,973; Belgian Pat. Offenlegungsschrift No. 832,227; Japanese Pat. Offenlegungsschrift No. 6,925/'76; ibid. 26,819/'76; ibid. 17,423/'77; Ring Doc, 13472P (Derwent Publications Ltd.), 1974; Cancer Treatment Reports, 60 (1976), 801; Cancer Research, 33 (1973), 2005; Proceeding of the Society for Experimental Biology and Medicine, 152 (1976), 195; Gann, 66 (1975), 347; ibid. 67 (1976), 137].

However, it is known that when GANU is produced by the above conventional nitrosating process for producing the glucopyranosenitrosourea compounds of formula I, the isomer having a nitroso group at the $N_3$-position, that is, the glucopyranose-nitrosourea compound with an $N_1$-substituted-3-nitrosourea group of formula $$-\underset{NO}{N}CONH-R^8$$

wherein $R^8$ is as hereinbefore defined, is also formed as a by-product. The antitumor activity of this by-product is 0–30% of that of the desired compound of formula I (cf. op. cit.).

OBJECTS AND SUMMARY OF THE INVENTION

I have extensively tested the formation of the by-product isomer having a nitroso group at the $N_3$-position in the conventional nitrosating process, and have found that the formation of the unwanted isomer similarly occurs in the production of the other glucopyranose-nitrosourea compounds as well as of GANU. Furthermore, the separation of the unwanted by-product from the desired compounds of formula I not only requires complex procedures, but these complex procedures result in a lowering of the yield of the desired compounds of formula I through decomposition. I have now studied various alternative processes for producing the glucopyranose-nitrosourea compounds of general formula I other than the conventional nitrosating process, and have found that when an aminoglucopyranose compound is reacted with a substituted-phenyl N-substituted-N-nitrosocarbamate compound, the desired compounds of general formula I are produced selectively and at markedly high yields.

DETAILED DESCRIPTION OF THE INVENTION

Thus, according to one aspect of the present invention, there is provided a process for the production of compounds of the general formula I as hereinbefore defined, characterized by reacting an aminoglucopyranose compound having the following general formula:

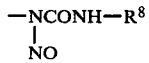 [IV]

[in which $R^4$ represents one member selected from the group consisting of hydroxy group, alkoxy group having from 1 to 4 carbon atoms, amino group (and acid-added amino group); and $R^5$ and $R^6$, which may be the same or different, each represents one member selected from the group consisting of hydroxy group, amino group (and acid-added amino group); with the proviso that $R^4$, $R^5$ and $R^6$ are not all the same], with a substituted-phenyl N-substituted-N-nitrosocarbamate compound having the following general formula:

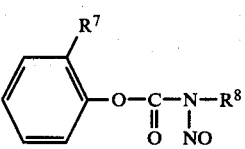

(in which $R^7$ represents a nitro or cyano group; and $R^8$ is as hereinbefore defined).

The process of the present invention enables the desired compounds of formula I to be prepared at a high rate, and further without the formation of unwanted isomers having a nitroso group at the $N_3$-position, thus allowing the desired compounds of formula I to be separated and refined by simple procedures, such as, for example, recrystallization 1 or 2 times which do not cause decomposition of the compounds of formula I.

The process of the present invention is believed to proceed according to the following reaction scheme:

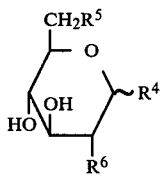

in which $R^1$, $R^2$, $R^3$, $R^4$, $R^5$, $R^6$, $R^7$ and $R^8$ are as hereinbefore defined.

Compounds having the general formula IV for use in the process of the present invention can be readily prepared by known methods. Compounds of formula IV are stable over a relatively wide range of temperatures, pH, and moisture contents, with the result that they may be stored for long terms.

Included within the scope of compounds of formula IV are the following four groups of compounds due to combinations of the substituting groups thereof:

Group (a): compounds wherein $R^4$ is hydroxy or alkoxy having 1 to 4 carbon atoms; $R^5$ is amino or an acid-added amino group and $R^6$ is hydroxy; that is, 6-amino-6-deoxy-D-glucopyranose, alkyl 6-amino-6-deoxy-D-glucopyranoside and their acid-addition salts;

Group (b): compounds wherein $R^4$ is hydroxy or alkoxy having 1 to 4 carbon atoms; and each of $R^5$ and $R^6$ is amino or an acid-added amino group; that is, 2,6-di-amino-2,6-di-deoxy-D-glucopyranose, alkyl 2,6-di-amino-2,6-di-deoxy-D-glucopyranoside and their acid-addition salts;

Group (c): compounds wherein $R^4$ is hydroxy or alkoxy having 1 to 4 carbon atoms; $R^5$ is hydroxy; and $R^6$ is amino or an acid-added amino group; that is, 2-amino-2-deoxy-D-glucopyranose, alkyl 2-amino-2-deoxy-D-glucopyranoside and their acid-addition salts; and Group (d): compounds wherein $R^4$ is amino or an acid-added amino group; and each of $R^5$ and $R^6$ is hydroxy; that is, 1-amino-1-deoxy-D-glucopyranose and its acid-addition salts.

Each of the above-mentioned compounds occurs in the form of two stereoisomers, that is, α-anomers and β-anomers. These anomers or mixtures thereof may be used as the starting materials in the process of the present invention.

Viewed from another aspect, the compounds of formula IV include three kinds of compounds, that is, amino-glucopyranose compounds (in the narrow sense), alkyl amino-glucopyranoside compounds (both being basic compounds) and acid-addition salts of these basic compounds. Of these three compound groups, the acid-addition salts are most preferred as the starting materials in the process of the present invention, in view of their stability as well as high formation rate of the desired compounds of formula I in the finished reaction. Said acid-addition salts are required, of course, to be able to maintain the substantial basicity of the reaction phase as far as the condensation-substitution reaction of the salts with the substituted-phenyl N-substituted-N-nitrosocarbamate compounds of formula V is effected sufficiently. Acids suitable for the formation of such acid-addition salts include organic acids such as, for example, formic acid, acetic acid, oxalic acid, lactic acid, fumaric acid, maleic acid, succinic acid and tartaric acid, or inorganic acids such as, for example, carbonic and cyanic acids, among which carbonic acid is most preferred.

The starting materials having the general formula V for use in the process of the present invention can also be readily prepared by known methods, and they are relatively stable at low temperatures. The compounds of formula V include, for example, o-nitrophenyl N-(2-chloroethyl)-N-nitrosocarbamate, o-cyanophenyl N-(2-chloroethyl)-N-nitrosocarbamate, o-nitrophenyl N-methyl-N-nitrosocarbamate, o-cyanophenyl N-methyl-N-nitrosocarbamate, o-nitrophenyl N-ethyl-N-nitrosocarbamate, o-nitrophenyl N-n-propyl-N-nitrosocarbamate and o-nitrophenyl N-n-butyl-N-nitrosocarbamate. Among others, o-nitrophenyl N-substituted-N-nitrosocarbamate is suitable in general, with respect to the yield of the desired compounds of formula I and the refinement of the same. The substituting groups at the phenyl nucleus of the compounds of formula V for use in the present invention have been selected on the basis of the speciality (or peculiarity) of condensation-substitution reaction thereof with the aforementioned compounds of formula IV. That is, we have tested the condensation-substitution reaction of the compounds of formula IV with many substituted-phenyl N-substituted-N-nitrosocarbamate compounds analogous to the compounds of formula V, for example, nitrosocarbamate compounds having p-nitro, p-chloro, o-chloro, p-methyl, 3,5-dimethyl, o-methyl, p-allyl, p-carbomethyl or p-acetyl groups in place of o-nitro and o-cyano groups at the phenyl nucleus of the compounds of formula V. These tests demonstrated that the desired glucopyranosenitrosourea compounds of formula I could not be obtained when the nitrosocarbamate compounds having groups other than nitro or cyano at the phenyl nucleus of formula V were used. This is perhaps due to the electron attractivity of such other groups being weaker than that of nitro and cyano groups. It was found further that when nitrosocarbamate compounds having a p-nitro or p-cyano group at the phenyl nucleus were used, although the desired compounds of formula I could be formed in the reaction, there was required to use very complex procedures, for example, column-chromatography for the separation of p-nitrophenol or p-cyanophenol, which had been formed similarly in the present condensation-substitution reaction, from the compounds of formula I formed therein. Furthermore, in such chromatography it was seen to give rise to a lowering of the overall yield of the compounds of formula I by 20–40% due to the unavoidable presence of a small amount of water in the adsorbent which had been employed in such chromatography. It is believed that the above-mentioned difficulty of separation of p-nitrophenol or p-cyanophenol from the compounds of formula I is due to a strong affinity between such p-substituted-phenols and the compounds of formula I, such strong affinity being a characteristic feature of the compounds of formula I.

The process of the present invention is advantageously effected in the presence of a suitable solvent at a temperature ranging between $-15°$ C. and the boiling temperature of said solvent. Particularly, when using the compounds of formula IV of Groups (a) and (b) above as starting materials, the temperature range is preferably between $-15°$ C. and $+60°$ C. When the compounds of formula IV of Group (c) are used as starting materials a temperature between $-15°$ C. and $+80°$ C. is preferred, while for the compounds of formula IV of Group (d) a temperature between $-15°$ C. and $+30°$ C. is preferred.

Convenient solvents in the process of the present invention are, for example, at least one compound selected from the group consisting of mono- or polyhydric alchols (aliphatic, alicyclic or aromatic) having from 1 to 12 carbon atoms, furans, nitriles, ketones, esters, ethers, amides, nitro-compounds, sulfur-containing compounds and phosphorus containing compounds. The solvent desirably has a moisture content of not more than 1% so as to prevent decomposition of the desired compound of formula I formed in the reaction. Among others, a solvent which is capable of either dissolving or dispersing both the starting materials or formulae IV and V therein is preferred. Such solvents include concretely methanol, ethanol, isopropanol (said three compounds are hereinafter generally called "lower alcohol"), tetrahydrofuran, toluene, dioxane, ethylacetate, dimethylformamide, dimethyl sulfoxide (said six compounds are hereinafter generally called "tetrahydrofuran, etc."), benzene, acetonitrile, methylene chloride, dimethylacetate, nitromethane, nitroethane, carbon disulfide and hexamethyl-phosphoramide; and mixture of one member selected from said lower alcohol with one member selected from the group consisting of said tetrahydrofuran, etc., benzene, acetonitrile, isopropyl ether, methylene chloride, carbon tetrachloride, nitromethane, nitroethane, dimethylacetamide, carbon disulfide and hexamethyl-phosphoramide; among which the solvent mixture is generally used advantageously. That is, more particularly, when the compounds of formula IV of Group (a) are used as starting materials, it is preferable to use mixture of one member selected from the lower alcohol with one member selected from the group consisting of the tetrahydrofuran, etc., benzene and isopropyl ether. When using the compounds of formula IV of Group (b) as starting materials, mixture of one member of the lower alcohol with one member selected from the group consisting of the tetrahydrofuran, etc. and acetonitrile is preferred. For the compounds of formula IV of Group (c), mixture of one member of the lower alcohol with one member selected from the group consisting of the tetrahydrofuran, etc., benzene, methylene chloride and carbon tetrachloride is preferred, while for the compounds of formula IV of Group (d), mixture of one member of the lower alcohol with one member selected from the group consisting of tetrahydrofuran, dioxane, dimethylformamide, benzene and ethylacetate is preferred.

In an embodiment of the process of the present invention, the final compounds of formula I formed in the reaction may be readily, after removal of the reaction solvents therefrom, separated and refined by 1 to 2 recrystallizations using suitable solvents. Such refining solvents include the lower alcohol and mixture of methanol or ethanol with one member selected from the group consisting of ethyl ether, petroleum ether, chloroform, ligroin, methylene chloride, n-hexane, acetone and methyl ethyl ketone. These refining solvents should desirably also have a moisture content of not more than 1%.

According to the present invention, various kinds of glucopyranose-nitrosourea compounds having the general formula I may be produced by the condensation-substitution reaction of the compounds of formulae IV and V which have various kinds of groups for $R^4$, $R^5$, $R^6$, $R^7$ and $R^8$. These glucopyranose-nitrosourea compounds of formula I may be classified into the following seven groups:

Group A:

1-(alkyl or 2-chloroethyl)-3-(alkyl D-glucopyranose-6-yl)-1-nitrosourea compounds, for example,
6MCαG,
3-(methyl β-D-glucopyranos-6-yl)-1-(2-chloroethyl)-1-nitrosourea,
3-(ethyl α-D-glucopyranos-6-yl)-1-(2-chloroethyl)-1-nitrosourea,
3-(ethyl β-D-glucopyranos-6-yl)-1-(2-chloroethyl)-1-nitrosourea,
3-(n-propyl α-D-glucopyranos-6-yl)-1-(2-chloroethyl)-1-nitrosourea,
3-(n-propyl β-D-glucopyranos-6-yl)-1-(2-chloroethyl)-1-nitrosourea,
3-(n-butyl α-D-glucopyranos-6-yl)-1-(2-chloroethyl)-1-nitrosourea,
3-(n-butyl β-D-glucopyranos-6-yl)-1-(2-chloroethyl)-1-nitrosourea,
3-(methyl α-D-glucopyranos-6-yl)-1-methyl-1-nitrosourea,
3-(methyl β-D-glucopyranos-6-yl)-1-methyl-1-nitrosourea,
3-(ethyl α-D-glucopyranos-6-yl)-1-methyl-1-nitrosourea,
3-(ethyl β-D-glucopyranos-6-yl)-1-methyl-1-nitrosourea,
3-(ethyl α-D-glucopyranos-6-yl)-1-ethyl-1-nitrosourea,
3-(ethyl β-D-glucopyranos-6-yl)-1-ethyl-1-nitrosourea, and
3-(n-propyl α-D-glucopyranos-6-yl)-1-n-butyl-1-nitrosourea;

Group B:

1-(alkyl or 2-chloroethyl)-3-(alkyl D-glucopyranos-2-yl)-1-nitrosourea compounds, for example,
2MCαG,
3-(methyl β-D-glucopyranos-2-yl)-1-(2-chloroethyl)-1-nitrosourea,
3-(ethyl α-D-glucopyranos-2-yl)-1-(2-chloroethyl)-1-nitrosourea,
3-(ethyl β-D-glucopyranos-2-yl)-1-(2-chloroethyl)-1-nitrosourea,
3-(n-propyl α-D-glucopyranos-2-yl)-1-(2-chloroethyl)-1-nitrosourea,
3-(n-propyl β-D-glucopyranos-2-yl)-1-(2-chloroethyl)-1-nitrosourea,
3-(n-butyl α-D-glucopyranos-2-yl)-1-(2-chloroethyl)-1-nitrosourea,
3-(n-butyl β-D-glucopyranos-2-yl)-1-(2-chloroethyl)-1-nitrosourea,
3-(methyl α-D-glucopyranos-2-yl)-1-methyl-1-nitrosourea,
3-(methyl β-D-glucopyranos-2-yl)-1-methyl-1-nitrosourea,
3-(methyl β-D-glucopyranos-2-yl)-1-ethyl-1-nitrosourea,
3-(methyl α-D-glucopyranos-2-yl)-1-n-propyl--nitrosourea,
3-(ethylα-D-glucopyranos-2-yl)-1-ethyl-1-nitrosourea,
3-(ethyl β-D-glucopyranos-2-yl)-1-ethyl-1-nitrosourea,
3-(n-propyl α-D-glucopyranos-2-yl)-1-methyl-1-nitrosourea, and
3-(n-butyl β-D-glucopyranos-2-yl)-1-methyl-1-nitrosourea;

Group C:

3,3'-(alkyl D-glucopyranos-2,6-di-yl)-bis[1-(alkyl or 2-chloroethyl)-1-nitrosourea] compounds, for example,
WMCαG,
3,3'-(methyl β-D-glucopyranos-2,6-di-yl)-bis[1-(2-chloroethyl)-1-nitrosourea],
3,3'-(ethyl α-D-glucopyranos-2,6-di-yl)-bis[1-(2-chloroethyl)-1-nitrosourea],
3,3'-(ethyl β-D-glucopyranos-2,6-di-yl)-bis[1-(2-chloroethyl)-1-nitrosourea],
3,3'-(n-propyl α-D-glucopyranos-2,6-di-yl)-bis[1-(2-chloroethyl)-1-nitrosourea],
3,3'-(n-propyl β-D-glucopyranos-2,6-di-yl)-bis[1(2-chloroethyl)-1-nitrosourea],
3,3'-(n-butyl α-D-glucopyranos-2,6-di-yl)-bis[1-(2-chloroethyl)-1-nitrosourea],
3,3'-(n-butyl β-D-glucopyranos-2,6-di-yl)-bis[1-(2-chloroethyl)-1-nitrosourea],
3,3'-(methyl α-D-glucopyranos-2,6-di-yl)-bis(1-methyl-1-nitrosourea),
3,3'-(methyl β-D-glucopyranos-2,6-di-yl)-bis(1-methyl-1-nitrosourea),
3,3'-(ethyl α-D-glucopyranos-2,6-di-yl)-bis(1-methyl-1-nitrosourea),
3,3'-(n-propyl α-D-glucopyranos-2,6-di-yl)-bis(1-methyl-1-nitrosourea),
3,3'-(n-butyl β-D-glucopyranos-2,6-di-yl)-bis(1-methyl-1-nitrosourea),
3,3'-(methyl α-D-glucopyranos-2,6-di-yl)-bis(1-ethyl-1-nitrosourea), and
3,3'-(n-propyl β-D-glucopyranos-2,6-di-yl)-bis(1-n-propyl-1-nitrosourea);

Group D:

1-(alkyl or 2-chloroethyl)-3-(D-glucopyranos-2-yl)-1-nitrosourea compounds, for example,
DCNU,
3-(D-glucopyranos-2-yl)-1-methyl-1-nitrosourea (i.e. SZ),
3-(D-glucopyranos-2-yl)-1-ethyl-1-nitrosourea,
3-(D-glucopyranos-2-yl)-1-n-propyl-1-nitrosourea, and
3-(D-glucopyranos-2-yl)-1-n-butyl-1-nitrosourea;

Group E:
  1-(alkyl or 2-chloroethyl)-3-(D-glucopyranos-6-yl)-1-nitrosourea compounds, for example,
    3-(D-glucopyranos-6-yl)-1-(2-chloroethyl)-1-nitrosourea (referred to as "6DCNU"),
    3-(D-glucopyranos-6-yl)-1-methyl-1-nitrosourea,
    3-(D-glucopyranos-6-yl)-1-ethyl-1-nitrosourea,
    3-(D-glucopyranos-6-yl)-1-n-propyl-1-nitrosourea, and
    3-(D-glucopyranos-6-yl)-1-n-butyl-1-nitrosourea;
Group F:
  1-(alkyl or 2-chloroethyl)-3-(D-glucopyranosyl)-1-nitrosourea compounds, for example,
    GANU,
    3-(β-D-glucopyranosyl)-1-methyl-1-nitrosourea,
    3-(β-D-glucopyranosyl)-1-ethyl-1-nitrosourea,
    3-(β-D-glucopyranosyl)-1-n-propyl-1-nitrosourea,
    3-(β-D-glucopyranosyl)-1-n-butyl-1-nitrosourea,
    3-(α-D-glucopyranosyl)-1-methyl-1-nitrosourea, and
    3-(α-D-glucopyranosyl)-1-ethyl-1-nitrosourea; and
Group G:
  3,3'-(D-glucopyranos-2,6-di-yl)-bis[1-(alkyl or 2-chloroethyl)-1-nitrosourea] compounds, for example,
    3,3'-(D-glucopyranos-2,6-di-yl)-bis[1-(2-chloroethyl)-1-nitrosourea],
    3,3'-(D-glucopyranos-2,6-di-yl)-bis(1-methyl-1-nitrosourea),
    3,3'-(D-glucopyranos-2,6-di-yl)-bis(1-ethyl-1-nitrosourea),
    3,3'-(D-glucopyranos-2,6-di-yl)-bis(1-n-propyl-1-nitrosourea), and
    3,3'-(D-glucopyranos-2,6-di-yl)-bis(1-n-butyl-1-nitrosourea).

The glucopyranose-nitrosourea compounds of formula I mentioned above have all exhibited an antitumor activity. The compounds of formula I of Groups A, C, D, F and G tend to decompose in the presence of a little water under acidic or neutral conditions, and also decompose regardless of the existence of water under basic conditions. Furthermore, these particular compounds tend to undergo intramolecular-condensation, so that it has hitherto been difficult to produce these compounds by the conventional nitrosating process at high yield. However, according to the process of the present invention, these compounds may be produced at high yield.

The compounds of formula I of Group E are novel, having not hitherto been synthesized, which compounds may be produced in the process of the present invention using the compounds of formula IV as the starting materials wherein $R^5$ is amino or an acid-added amino group and each of $R^4$ and $R^6$ is hydroxy.

Tests comparing physical and pharmacological properties of SZ (a compound of Group D), DCNU (a compound of Group D), GANU (a compound of Group F), 2MCαG (a compound of Group B), 6MCαG (a compound of Group A) and 6DCNU (a compound of Group E) were carried out and the results are hereinafter.

(1) SOLUBILITY IN WATER

Table I shows amounts (mg) of the test compounds soluble in 1 ml water at 25° C. From the Table, it may be seen that the solubility of 6DCNU is higher than that of both DCNU and 2MCαG and is almost equal to that of 6MCαG.

Table 1

| Test Compound | Solubility (mg) |
|---|---|
| 6DCNU | 750 |
| DCNU | 40 |
| 2MCαG | 45 |
| 6MCαG | 900 |

(2) ANTITUMOR ACTIVITY

Test compounds were given to BDF$_1$ mice 24 hrs after implantation of $10^6$ cells of leukemia L-1210 in each animal, through single intraperitoneal administration, intraperitoneal administration for 5 successive days, single oral administration or oral administration for 5 successive days, whereupon the increase in life span (referred to as "ILS") and number of 60 days survivors of test animals were estimated, said test of antitumor activity being that according to the method of the National Cancer Center, Tokyo [A. Hoshi et al: Farmashia, 9 (1973), 464]. In the tests, the compounds were dissolved in physiological saline solution just before administration. Results are shown in Table II, from which it can be seen that the antitumor activity of 6DCNU is superior to that of DCNU, GANU and 2MCαG, and is almost equal to that of 6MCαG, and further that 6DCNU exhibits a high activity equal to that of 6MCαG in oral administration.

Table II

| Test Compound | Dosage (mg/kg/day) | Treatment[a] | ILS[b] (%) | Survivors[c] |
|---|---|---|---|---|
| 6DCNU | 12.5 | i.p. D$_1$ | >426 | 4/6 |
| | 25.0 | | >561 | 5/6 |
| | 50.0 | | >606 | 5/6 |
| | 70.0 | | >321 | 3/6 |
| | 100.0 | | −3 | |
| | 150.0 | | −10 | |
| | 200.0 | | −34 | |
| | 3.2 | i.p. D$_{1\sim5}$ | >310 | 2/6 |
| | 6.3 | | >410 | 4/6 |
| | 12.5 | | >520 | 5/6 |
| | 15.0 | | >650 | 6/6 |
| | 20.0 | | >670 | 6/6 |
| | 25.0 | | >540 | 5/6 |
| | 30.0 | | >315 | 3/6 |
| | 40.0 | | >225 | 2/6 |
| | 12.5 | p.o. D$_{1\sim5}$ | >123 | |
| | 25.0 | | >260 | 2/6 |
| | 35.0 | | >390 | 3/6 |
| | 50.0 | | >442 | 3/6 |
| | 70.0 | | >370 | 3/6 |
| | 100.0 | | >246 | 2/6 |
| DCNU | 6.3 | i.p. D$_1$ | >265 | 3/6 |
| | 12.5 | | >418 | 4/6 |
| | 25.0 | | >315 | 3/6 |
| | 50.0 | | −10 | |
| DCNU | 1.6 | i.p. D$_{1\sim5}$ | >143 | 1/6 |
| | 3.2 | | >407 | 3/6 |
| | 4.5 | | >406 | 3/6 |
| | 6.3 | | >622 | 5/6 |
| | 9.0 | | >153 | 1/6 |
| | 1.6 | p.o. D$_{1\sim5}$ | −10 | |
| | 3.2 | | 6 | |
| | 6.3 | | 13 | |
| | 12.5 | | 13 | |
| | 25.0 | | 13 | |
| | 50.0 | | 15 | |
| | 100.0 | | 18 | |
| | 200.0 | | −23 | |
| 2MCαG | 6.3 | i.p. D$_1$ | >128 | |
| | 8.0 | | >432 | 3/6 |
| | 10.0 | | >717 | 6/6 |
| | 20.0 | | >717 | 6/6 |
| | 25.0 | | >539 | 4/6 |
| | 0.5 | i.p. D$_{1\sim5}$ | 15 | |
| | 1.0 | | 48 | |
| | 2.0 | | >249 | 1/6 |

Table II-continued

| Test Compound | Dosage (mg/kg/day) | Treatment[a] | ILS[b] (%) | Survivors[c] |
|---|---|---|---|---|
| | 3.2 | | >394 | 3/6 |
| | 4.0 | | >349 | 2/6 |
| | 6.3 | | >198 | 1/6 |
| | 10.0 | | >190 | 1/6 |
| | 12.5 | | >160 | 1.6 |
| | 20.0 | | 58 | |
| | 2.0 | p.o. $D_{1\sim 5}$ | >143 | 1/6 |
| | 3.2 | | >246 | 2/6 |
| | 6.3 | | >380 | 3/6 |
| | 12.5 | | >211 | 2/6 |
| 6MCαG | 6.3 | i.p. $D_1$ | >241 | 3/6 |
| | 9.0 | | >604 | 5/6 |
| | 12.5 | | >619 | 6/6 |
| | 18.0 | | >632 | 6/6 |
| | 25.0 | | >625 | 6/6 |
| | 35.0 | | >632 | 6/6 |
| | 50.0 | | >388 | 3/6 |
| | 2.3 | i.p. $D_{1\sim 5}$ | >207 | 1/6 |
| | 3.2 | | >521 | 4/6 |
| | 4.5 | | >607 | 5/6 |
| | 6.3 | | >722 | 6/6 |
| 9.0 | | | >700 | 6/6 |
| | 12.5 | | >722 | 6/6 |
| | 18.0 | | >493 | 4/6 |
| | 25.0 | | >393 | 3/6 |
| | 35.0 | | >157 | 1/6 |
| | 3.2 | p.o. $D_{1\sim 5}$ | 38 | |
| | 6.3 | | >397 | 3/6 |
| | 9.0 | | >417 | 3/6 |
| | 12.5 | | >700 | 6/6 |
| | 18.0 | | >679 | 6/6 |
| | 25.0 | | 233 | |
| GANU | 1.0 | i.p. $D_1$ | 42 | |
| | 5.0 | | >280 | 2/6 |
| | 10.0 | | >295 | 2/6 |
| | 15.0 | | >507 | 5/6 |
| | 20.0 | | >518 | 5/6 |
| | 25.0 | | >472 | 5/6 |
| | 5.0 | p.o. $D_1$ | 5 | |
| | 10.0 | | 45 | |
| | 20.0 | | 75 | |
| | 25.0 | | 110 | |
| | 35.0 | | 70 | |

[a] i.p.: intraperitoneal administration p.o: oral administration $D_1$: single administration $D_{1\sim 5}$: administration for 5 successive days
[b] percentage calculated from mean survival time over control
[c] survivors/six animals

(3) DIABETOGENIC ACTIVITY

40–96 mg/kg of the test compounds were administered intravenously to starved male Wister rats weighing 240–260 g each, and the blood glucose concentrations of the test animals were estimated by the glucose exidase method [L. L. Saloman et al: Anal. Chem., 31 (1959), 453], in which test the compounds were dissolved in physiological saline solution just before administration. Results of the test are shown in Table III, from which it can be seen that 6DCNU, 2MCαG and 6MCαG produce substantially the same blood glucose concentrations as that in the control.

It should be noted here that 6DCNU has produced low diabetogenic activity as mentioned above. The diabetogenic activity of the known glucopyranose-nitrosourea compounds of formula I having antitumor activity is generally seen to decrease in order SZ>DCNU>GANU> 2MCαG≈6MCαG, and this property has hitherto been understood to be due to the difference of chemical structures of these compounds. That is, the hydroxy group at the 1-position carbon of the D-glucopyranose skeleton of these compounds is free (in SZ and DCNU), alkylated (in 2MCαG, 6MCαG and WMCαG) or substituted with 1-(2-chloroethyl)-1-nitrosourea group (in GANU). In other words, it has been believed that the hydroxy group at the 1-position carbon of D-glucopyranose skeleton should be substituted with any other group for the purpose of lowering the diabetogenic activity of the compounds of formula I. I have now found that in spite of the hydroxy group at the 1-position carbon of D-glucopyranose skeleton of the novel 6DCNU being free, the 6-position carbon of D-glucopyranose skeleton of which 6DCNU is combined with 1-(2-chloroethyl)-1-nitrosourea group, this novel compound not only has a low diabetogenic activity, but also has an excellent antitumor activity. In consequence, my discovery of the novel compounds of formula I of Group E may be regarded as having changed the conventional concepts concerning the relation of physiological activity of the glucopyranose-nitrosourea compounds of formula I with the chemical structure thereof.

Table III

| Time after treatment (hr) | Saline water | 6DCNU (mg/kg) | | | SZ (mg/kg) | | DCNU (mg/kg) | | | GANU (mg/kg) | | 2MCαG (mg/kg) | | 6MCαG (mg/kg) | | |
|---|---|---|---|---|---|---|---|---|---|---|---|---|---|---|---|---|
| | | 40 | 60 | 77 | 40 | 60 | 40 | 60 | 80 | 40 | 60 | 40 | 60 | 40 | 60 | 80 |
| 0 | 67.2 | 70.4 | 72.0 | 72.4 | 68.2 | 67.8 | 67.5 | 68.2 | 70.5 | 67.8 | 67.3 | 71.0 | 70.4 | 72.0 | 71.8 | 73.7 |
| 2 | 72.4 | 73.3 | 74.2 | 75.3 | 98.4 | 100.8 | 87.2 | 88.4 | 90.3 | 70.4 | 71.2 | 73.5 | 74.2 | 75.9 | 72.5 | 82.0 |
| 4 | 76.5 | 67.7 | 78.3 | 75.8 | 117.2 | 123.8 | 74.6 | 72.4 | 68.6 | 71.3 | 72.6 | 70.6 | 68.2 | 79.3 | 69.8 | 78.3 |
| 7 | 78.6 | 68.2 | 76.8 | 79.8 | 63.6 | 56.4 | 85.3 | 92.1 | 93.7 | 94.4 | 95.4 | 72.3 | 68.7 | 71.7 | 68.7 | 77.8 |
| 10 | 80.2 | 68.3 | 79.2 | 76.2 | 46.5 | 42.5 | 110.2 | 115.7 | 123.5 | 98.2 | 105.9 | 68.3 | 67.5 | 79.4 | 67.7 | 73.6 |
| 24 | 78.7 | 69.9 | 78.7 | 78.2 | 183.8 | 195.4 | 142.2 | 162.6 | 178.7 | 120.3 | 125.5 | 72.7 | 73.8 | 73.1 | 68.4 | 76.3 |
| 48 | 77.3 | 73.8 | 79.4 | 80.5 | 246.2 | 248.8 | 229.4 | 242.3 | 264.8 | 186.5 | 189.8 | 70.4 | 70.8 | 75.3 | 70.8 | 83.1 |

Blood Glucose Concentration (mg/dl)

(4) ACUTE TOXICITY ($LD_{50}$)

Test compounds were dissolved in physiological saline solution just before their dosage and administered to male Wister rats, intraperitoneally, intravenously and orally. After 1 week, the $LD_{50}$ of each compound was calculated from the mortality of the test animals by the Lichfield-Wilcoxon Method. Results are shown in Table IV, from which it is seen that the $LD_{50}$ value of 6DCNU is higher than that of the other known compounds. Incidentally, although it is seen from Table IV that the $LD_{50}$ value of DCNU in oral administration is markedly high (1,149 mg/kg), this result is considered to be due to this compound being decomposed orally in view of the fact that DCNU appears to show no antitumor activity in oral administration (cf. Table II).

Table IV

| Test Compound | $LD_{50}$ (mg/kg) | |
|---|---|---|
| 6DCNU | 90 | i.p. |
| | 85 | i.v. |
| | 132 | p.o. |
| DCNU | 44 | i.p. |
| | 1149 | p.o. |
| 2MCαG | 48 | i.p. |
| | 49 | p.o. |

Table IV-continued

| Test Compound | LD$_{50}$ (mg/kg) | |
|---|---|---|
| 6MCαG | 42 | i.p. |
| | 42 | i.v. |
| | 50 | p.o. |
| GANU | 24 | i.p. |
| | 10 | i.v. |
| | 21 | p.o. | i.v.: intravenous administration

(5) EFFECT ON RESPIRATION, BLOOD PRESSURE, HEART RATE AND ELECTROCARDIOGRAM

Beagle dogs of both sexes weighing about 10 kg were anesthetized with pentobarbital sodium (30 mg/kg, i.v.), and immobilized in the supine position. Test compounds dissolved in physiological saline solution were injected into the brachial veins of the animals and the arteries at cannulated positions were treated with heparin sodium as anticoagulant.

The respiration rate of each animal was estimated with a respirometer (Nihonkohden, RP-3) through a tracheal cannula, the blood pressure with an electro-haemodynamometer (Nihonkohden, MP-4T) attached surgically to the femoral artery, and the heart rate with a pulse-rate tachometer (Nihonkohden, RT-2) through the trigger pulse of the blood pressure. These data were all recorded by an ink-writing oscillograph (Nihonkohden, WI-380), while the electrocardiogram (lead II) was recorded with an electrocardiograph (Nihonkohden, MC-12). Table V shows the maximum dosages of test compounds not effected on respiration, blood pressure, heart rate and electrocardiogram of the animals, which reveals that 6DCNU shows the highest dosage value.

Table V

| Test Compound | Dosage (mg/kg) |
|---|---|
| 6DCNU | 70 |
| DCNU | 20 |
| 2MCαG | 30 |
| 6MCαG | 50 |
| GANU | 10 |

(6) ABSORPTION AND EXCRETION

The carbon atom at the 2-position of the chloroethyl group (i.e. ClCH$_2$CH$_2$-) of 6DCNU and 6MCαG was labelled with radioactive $^{14}$C, and the absorption and excretion of these compounds were tested using rats. The results of the test were as follows: both compounds were absorbed well and excreted mainly in the urine; intravenous and oral administrations showed almost the same excretion rates; in 6MCαG-$^{14}$C, 50-60% and 80-90% of the dose were excreted in urine within 12 hours and 96 hours after the dose respectively, while 5-6% of the dose was excreted in faeces within 96 hours and 3-4% in expiration within 24 hours; on the other hand, in 6DCNU-$^{14}$C, 65-70% and 75-80% of the dose were excreted in urine within 12 hours and 72 hours after the dose respectively, while 10-15% of the dose was excreted in faeces within 72 hours and 3-5% in expiration within 24 hours. From the above data, it is seen that 6DCNU is excreted more than 6MCαG in faeces and further that the excretion velocity of 6DCNU is more rapid than that of 6MCαG, said situation showing that 6DCNU is less toxic than 6MCαG.

(7) ANTIBACTERIAL ACTIVITY

Using 6DCNU and 6MCαG, minimum inhibiting concentrations (referred to as "MIC") for various kinds of bacteria were estimated by means of the broth-dilution method. Results are shown in Table VI, which reveals that both the test compounds have no substantial antibacterial activity.

Table VI

| Bacteria tested | MIC (μg/ml) 6MCαG | 6DCNU |
|---|---|---|
| Bacillus subtilis ATCC 6633 | >200 | >200 |
| Escherichia coli NIHJ JC-2 | >200 | >200 |
| Klebsiella pneumoniae IFM 3008 | >200 | >200 |
| Mycobacterium smegmatis ATCC 607 | >200 | >200 |
| Proteus vulgaris AHU 1469 | >200 | >200 |
| Pseudomonas aeruginosa IFO 3080 | >200 | >200 |
| Shigella sonnei | >200 | >200 |
| Sarcina lutea ATCC 9341 | >200 | >200 |
| Staphylococcus aureus FDA 209P JC-1 | >200 | >200 |
| Streptococcus faecalis AHU 1085 | >200 | >200 |

The new compounds of formula II, for example, 6DCNU, of this invention, have, as indicated above, excellent physical and pharmacological properties, so that the compounds of formula II may, similarly to conventional useful compounds having antitumor activity, be formulated into pharmaceutical compositions by mixing with physiologically acceptable solid or liquid carriers. The compositions may, for example, take the form of injections, tablets, coated tablets, capsules, powders, granules, solutions, emulsions or suppositories.

The carriers for use in such compositions may, for example, be those conventionally used for such forms and may include fillers (or binders) or disintegrants such as, for example, starch, dextrine, glucose, lactose, sucrose, methyl cellulose, calcium carboxymethyl cellulose, crystalline cellulose, magnesium stearate, sodium alginate, Witepsol E85, Witepsol W35, and polyvinyl alcohol; lubricants such as, for example, talc, stearic acid, waxes, hydroxypropyl cellulose, and boric acid; coating materials such as, for example, Shellac, cellulose acetate-phthalate, and polyvinyl acetal diethylaminoacetate; solubilizers such as, for example, glycerin, propylene glycol, and mannitol; emulsifiers or suspending agents such as, for example, polyoxyethylene stearate, polyoxyethylene cetylalcohol ether, gum arabic, and soda soap; stabilizers such as, for example, sorbitol, Tween 80, Span 60, and fats and oils; and solvents of many kinds.

The amount of the compound of formula II included in a single dosage unit of said pharmaceutical composition may, for example, be 1-1000 mg/kg for injection solutions, 10-500 mg/kg for oral dosage units and 5-1000 mg/kg for suppositories. Examples of the compositions are as follows:-

| Intravenous-drip injections | | |
|---|---|---|
| i) 6DCNU | 180 | mg |
| physiological saline water | 300 | ml |
| ii) 6DCNU | 180 | mg |
| electrolyte | 200 | ml |
| iii) 6DCNU | 50 | mg |
| mannitol | 125 | " |
| Intravenous injections | | |
| i) 6DCNU | 50 | mg |
| mannitol | 100 | " |
| ii) 6DCNU | 30 | mg |
| lactose | 30 | " |

| -continued | | |
|---|---:|---|
| iii) 6DCNU | 50 | " |
| physiological saline water | 5 | ml |
| Tablets | | |
| 6DCNU | 150 | mg |
| crystalline cellulose | 45 | " |
| starch | 25 | " |
| lactose | 48 | mg |
| calcium carboxymethyl cellulose | 25 | " |
| magnesium stearate | 2 | " |
| hydroxypropyl cellulose | 5 | " |
| Total | 300 | mg |
| Granules | | |
| 6DCNU | 150 | mg |
| crystalline cellulose | 20 | " |
| starch | 20 | " |
| lactose | 40 | " |
| calcium carboxymethyl cellulose | 15 | " |
| hydroxypropyl cellulose | 5 | " |
| Total 250 | | mg |
| Capsules | | |
| 6DCNU | 100 | mg |
| crystalline cellulose | 20 | " |
| starch | 18 | " |
| lactose | 40 | " |
| calcium carboxymethyl cellulose | 15 | " |
| hydroxypropyl cellulose | 5 | " |
| magnesium stearate | 2 | " |
| Total | 200 | mg |
| Suppositories | | |
| i) Witepsol W35 | 830 | mg |
| Witepsol E85 | 82 | " |
| polyoxyethylene stearate | 48 | " |
| 6DCNU | 340 | " |
| Total | 1300 | mg |
| ii) Witepsol W35 | 830 | mg |
| Witepsol E85 | 82 | " |
| polyoxyethylene cetylalcohol ether | 48 | " |
| 6DCNU | 340 | " |
| Total | 1300 | mg |

Total

The following Examples serve to illustrate the invention without however limiting it in any way. Throughout the Examples, the solvents mentioned without the adjective "anhydrous" refer to those having a moisture content of not more than 1%.

EXAMPLE 1

6.80 g (24.8 mmol) of o-nitrophenyl N-(2-chloroethyl)-N-nitrosocarbamate is dissolved in 55 ml of anhydrous tetrahydrofuran, and the solution is cooled to a temperature of 0°–5° C. To this solution is added dropwise a solution prepared by dissolving 4.35 g (22.5 mmol) of methyl 6-amino-6-deoxy-α-D-glucopyranoside in 24 ml of anhydrous methanol, while stirring, at 20°–25° C. over 10 minutes. The resultant mixture is stirred at the same temperature for a further 1.5 hours. The thus reacted solution is concentrated at 40° C. and below, under reduced pressure. The crystalline residue obtained is washed with anhydrous ethyl ether, dried under reduced pressure, and recrystallized from anhydrous ethanol-ethyl ether (1:1) to give 6.11 g of 3-(methyl α-D-glucopyranos-6-yl)-1-(2-chloroethyl)-1-nitrosourea as pale yellowish needles. Yield 82.9%. mp 111°–112° C. (decomp.). $[\alpha]_D^{20}$ +93.2° (C 0.5, methanol). Analysis for $C_{10}H_{18}N_3O_7Cl$ (MW 327.72):

Calcd. (%) C, 36.65; H, 5.54; N, 12.82; Cl, 10.82. Found (%) C, 36.60; H, 5.48; N, 12.84; Cl, 10.80.

EXAMPLE 2

3.11 g (12.2 mmol) of o-cyanophenyl N-(2-chloroethyl)-N-nitrosocarbamate is dissolved in 15 ml of anhydrous dioxane, and to this solution is added dropwise a solution prepared by dissolving (partially suspending) 1.93 g (10.0 mmol) of methyl 6-amino-6-deoxy-α-D-glucopyranoside in 15 ml of anhydrous ethanol, while stirring, at about 25° C. over 10 minutes. The resultant mixture is stirred at the same temperature for a further 2 hours. The thus reacted solution is concentrated at 40° C. and below, under reduced pressure. The crystalline residue obtained is washed with anhydrous ethyl ether, dried under reduced pressure, and recrystallized from anhydrous ethanol-ethyl ether (1:1) to give 2.61 g of 3-(methyl α-D-glucopyranos-6-yl)-1-(2-chloroethyl)-1-nitrosourea as pale yellowish needles. Yield 79.6%. mp 111°–112° C. (decomp.). $[\alpha]_D^{25}$ +96.2° (C 0.5, methanol).

Analysis for $C_{10}H_{18}N_3O_7Cl$ (MW 327.72): Calcd. (%) C, 36.65; H, 5.54; N, 12.82; Cl, 10.82. Found (%) C, 36.61; H, 5.58; N, 12.90; Cl, 10.86.

EXAMPLE 3

1.93 g (10.0 mmol) of methyl 6-amino-6-deoxy-β-D-glucopyranoside is dissolved (partially suspended) in 20 ml of anhydrous ethanol, and this solution is added dropwise to a solution prepared by dissolving 3.56 g (13 mmol) of o-nitrophenyl N-(2-chloroethyl)-N-nitrosocarbamate in 15 ml of anhydrous tetrahydrofuran, while stirring, at 25°–26° C. over 10 minutes. The resultant mixture is stirred at the same temperature for a further hour. The thus reacted solution is concentrated at 30° C. and below, under reduced pressure. The crystalline residue obtained is washed with petroleum ether and then with ethyl ether, dried under reduced pressure, and recrystallized from anhydrous ethanol to give 2.65 g of 3-(methyl β-D-glucopyranos-6-yl)-1-(2-chloroethyl)-1-nitrosourea. Yield 81.0%. mp 121°–123° C. (decomp.). $[\alpha]_D^{25}$ −6° (C 0.3, methanol).

Analysis for $C_{10}H_{18}N_3O_7Cl$ (MW 327.72): Calcd. (%) C, 36.65; H, 5.54; N, 12.82; Cl, 10.82. Found (%) C, 36.72; H, 5.62; N, 12.78; Cl, 10.74.

EXAMPLE 4

1.79 g (10.0 mmol) of 6-amino-6-deoxy-D-glucopyranose is dissolved in a mixture of 15 ml methanol and 5 ml dimethyl sulfoxide, and the solution is cooled to 0°–5° C. This solution is added dropwise to a solution prepared by dissolving 3.28 g (12.0 mmol) of o-nitrophenyl N-(2-chloroethyl)-N-nitrosocarbamate in 20 ml of tetrahydrofuran, while stirring, at 0°–5° C. over 30 minutes. The resultant mixture is stirred at the same temperature for a further 2 hours. The thus reacted solution is concentrated at 30° C. and below, under reduced pressure. To the oily residue produced is added 100 ml of ethyl ether and the mixture is left at 4° C. overnight. The crystals thereby obtained are washed with chloroform and then with ethyl ether, dried under reduced pressure, and recrystallized from anhydrous ethanol-n-hexane (4:1) to give 2.33 g of 3-(D-glucopyranos-6-yl)-1-(2-chloroethyl)-1-nitrosourea. Yield 74.3%. mp 102°–103° C. (decomp.). $[\alpha]_D^{20}$ +55° (C 0.5, methanol; the value of +55° reduced to +31° after 22 hours). Analysis for $C_9H_{16}N_3O_7Cl$ (MW 313.69):

Calcd. (%) C, 34.46; H, 5.14; N, 13.40; Cl, 11.30. Found (%) C, 34.22; H, 5.08; N, 13.41; Cl, 11.35.

IR Spectrum (KBr, cm$^{-1}$): 1680 ($\nu$C=O), 1495 ($\nu$N=O); NMR Spectrum (DMSO-d$_6$, $\delta$): 3.60 (2H, triplet, CH$_2$CH$_2$Cl), 4.10 (2H, triplet, CH$_2$CH$_2$Cl), 8.25 (1H, triplet, NH)

EXAMPLE 5

2.07 g (10.0 mmol) of ethyl 6-amino-6-deoxy-$\alpha$-D-glucopyranoside is dissolved in a mixture of 10 ml dioxane and 10 ml anhydrous methanol, and this solution is added dropwise to a solution prepared by dissolving 3.43 g (12.5 mmol) of o-nitrophenyl N-(2-chloroethyl)-N-nitrosocarbamate in 15 ml tetrahydrofuran, while stirring, at 20°–22° C. over 10 minutes. The resultant mixture is stirred at the same temperature for a further hour. The thus reacted solution is concentrated at 40° C. and below, under reduced pressure. The crystalline residue obtained is washed with methyl ethyl ketone and further with ethyl ether, dried under reduced pressure, and recrystallized from ethanol to give 2.55 g of 3-(ethyl $\alpha$-D-glucopyranos-6-yl)-1-(2-chloroethyl)-1-nitrosourea. Yield 74.6%. mp 101°–103° C. (decomp.). $[\alpha]_D^{25}$ +113° (C 0.3, methanol). Analysis for C$_{11}$H$_{20}$N$_3$O$_7$Cl (MW 341.75):

Calcd. (%) C, 38.66; H, 5.90; N, 12.30; Cl, 10.37. Found (%) C, 38.74; H, 5.82; N, 12.22; Cl, 10.38.

EXAMPLE 6

3.28 g (12.0 mmol) of o-nitrophenyl N-(2-chloroethyl)-N-nitrosocarbamate is dissolved in 30 ml of tetrahydrofuran, and to this solution is added dropwise a solution prepared by dissolving (partially suspending) 2.35 g (10.0 mmol) of n-butyl 6-amino-6-deoxy-$\alpha$-D-glucopyranoside in 25 ml of ethanol, while stirring, at 20°–25° C. over 15 minutes. The resultant mixture is stirred at the same temperature for a further hour. The thus reacted solution is concentrated at 40° C. and below, under reduced pressure. The crystalline residue obtained is washed with n-hexane and further with ethyl ether, dried under reduced pressure, and recrystallized from anhydrous isopropanol to give 2.96 g of 3-(n-butyl $\alpha$-D-glucopyranos-6-yl)-1-(2-chloroethyl)-1-nitrosourea as pale yellowish crystals. Yield 80.0%. mp 107°–109° C. (decomp.). $[\alpha]_D^{25}$ +145° (C 0.5, methanol). Analysis for C$_{13}$H$_{24}$N$_3$O$_7$Cl (MW 369.80):

Calcd. (%) C, 42.22; H, 6.54; N, 11.36; Cl, 9.59. Found (%) C, 42.27; H, 6.60; N, 11.38; Cl, 9.60.

EXAMPLE 7

Analogously to Example 6 using 2.21 g (10 mmol) of n-propyl 6-amino-6-deoxy-$\alpha$-D-glucopyranoside in place of 2.35 g of n-butyl 6-amino-6-deoxy-$\alpha$-D-glucopyranoside, there is obtained 2.60 g of 3-(n-propyl $\alpha$-D-glucopyranos-6-yl)-1-(2-chloroethyl)-1-nitrosourea as pale yellowish crystals. Yield 73.0%. mp 93°–95° C. (decomp.). $[\alpha]_D^{25}$ +129° (C 0.5, methanol). Analysis for C$_{12}$H$_{22}$N$_3$O$_7$Cl (MW 355.77):

Calcd. (%) C, 40.51; H, 6.23; N, 11.81; Cl, 9.97. Found (%) C, 40.62; H, 6.18; N, 11.77; Cl, 9.92.

EXAMPLE 8

2.35 g (10 mmol) of n-butyl 6-amino-6-deoxy-$\alpha$-D-glucopyranoside is dissolved in a mixture of 25 ml methanol and 25 ml tetrahydrofuran, and to this solution is added 4.40 g (100 mmol) of dry-ice little by little so as to convert said glucopyranoside into its carbonic acid-addition salt. This acid-addition salt solution is then added dropwise to a solution, which has been prepared by dissolving 3.04 g (12 mmol) of o-cyanophenyl N-(2-chloroethyl)-N-nitrosocarbamate in a mixture of 13 ml tetrahydrofuran and 13 ml isopropyl ether and which has been cooled to 0°–5° C., while stirring, over 20 minutes. The resultant mixture is stirred further at 22°–25° C. for 2 hours. The thus reacted solution is concentrated at 40° C. and below, under reduced pressure. The crystalline residue obtained is washed with n-hexane and then with ethyl ether, dried under reduced pressure, and recrystallized from isopropanol to give 3.2 g of 3-(n-butyl $\alpha$-D-glucopyranos-6-yl)-1-(2-chloroethyl)-1-nitrosourea as pale yellowish crystals. Yield 86.5%. mp 107°–109° C. (decomp.). $[\alpha]_D^{25}$ +147° (C 0.5, methanol). Analysis for C$_{18}$H$_{24}$N$_3$O$_7$Cl (MW 369.80):

Calcd. (%) C, 42.22; H, 6.54; N, 11.36; Cl, 9.59. Found (%) C, 42.25; H, 6.71; N, 11.34; Cl, 9.61.

EXAMPLE 9

110.0 g (0.57 mmol) of methyl 6-amino-6-deoxy-$\alpha$-D-glucopyranoside is dissolved in 600 ml of methanol, and to this solution is added 75.3 g (1.71 mol) of dry-ice little by little so as to convert the glucopyranoside into its carbonic acid-addition salt. This acid-addition salt solution is then added dropwise to the solution which has been prepared by dissolving 172.0 g (0.63 mol) of o-nitrophenyl N-(2-chloroethyl)-N-nitrosocarbamate in 1000 ml of tetrahydrofuran and which has been cooled to 0°–5° C., while stirring, over an hour. The resultant mixture is stirred further at 22°–25° C. for 2 hours. The thus reacted solution is concentrated at 40° C. and below, under reduced pressure. The crystalline residue obtained is washed with ethyl ether, dried under reduced pressure, and recrystallized from ethanol-ligroin (4:1) to give 162.1 g of 3-(methyl $\alpha$-D-glucopyranos-6-yl)-1-(2-chloroethyl)-1-nitrosourea as pale yellowish needles. Yield 86.8%. mp 111°–112° C. (decomp.). $[\alpha]_D^{20}$ +93.2° (C 0.5, methanol).

Analysis for C$_{10}$H$_{18}$N$_3$O$_7$Cl (MW 327.72): Calcd. (%) C, 36.65; H, 5.54; N, 12.82; Cl, 10.82. Found (%) C, 36.67; H, 5.50; N, 12.80; Cl, 10.81.

EXAMPLE 10

1.93 g (10 mmol) of methyl 6-amino-6-deoxy-$\alpha$-D-glucopyranoside is dissolved (partially suspended) in 15 ml of ethanol, and to this solution is added 7.50 g (170 mmol) of dry-ice little by little so as to convert said glucopyranoside into its carbonic acid-addition salt. This acid-addition salt solution is then added dropwise to a solution prepared by dissolving 2.70 g (12 mmol) of o-nitrophenyl N-methyl-N-nitrosocarbamate in 10 ml of benzene, while stirring, at 20°–25° C. over 10 minutes. The resultant mixture is stirred at the same temperature for a further 1.5 hours. The thus reacted solution is concentrated at 40° C. and below, under reduced pressure. The crystalline residue obtained is washed with ethyl ether, dried under reduced pressure, and recrystallized from ethanol to give 2.41 g of 3-(methyl $\alpha$-D-glucopyranos-6-yl)-1-methyl-1-nitrosourea as pale yellowish crystals. Yield 86.4%. mp 143°–146° C. (decomp.). $[\alpha]_D^{25}$ +102° (C 0.5, water). Analysis for C$_9$H$_{17}$N$_3$O$_7$ (MW 279.25):

Calcd. (%) C, 38.71; H, 6.14; N, 15.05. Found (%) C, 38.96; H, 6.22; N, 14.91.

EXAMPLE 11

3.86 g (20 mmol) of methyl 6-amino-6-deoxy-D-glucopyranoside is dissolved in 20 ml of methanol, and this solution is added dropwise to a solution prepared by dissolving 6.55 g (23.9 mmol) of o-nitrophenyl N-(2-chloroethyl)-N-nitrosocarbamate in 50 ml of tetrahydrofuran, while stirring, at 20°–23° C. over 10 minutes. The resultant mixture is stirred at the same temperature for a further hour. The thus reacted solution is concentrated at 30° C. and below, under reduced pressure. The crystalline residue obtained is washed with 30 ml of ethyl ether, dried under reduced pressure, and dissolved in chloroform-ethanol (19:1). The resultant solution is subjected to column-chromatography [solid support: Kieselgel-60 (trademark); developing solvent: chloroform-ethanol (19:1)], to thereby fractionate it into α- and β-anomer fractions. Respective fractions are concentrated under reduced pressure and the crystalline residues obtained are recrystallized from ethanol to afford 2.04 g of 3-(methyl α-D-glucopyranos-6-yl)-1-(2-chloroethyl)-1-nitrosourea (referred to α-anomer) and 2.16 g of 3-(methyl β-D-glucopyranos-6-yl)-1-(2-chloroethyl)-1-nitrosourea (referred to β-anomer), respectively. For the α-anomer: yield 31.1%; mp 111°–113° C. (decomp.); $[α]_D^{25} +94°$ (C 1.0, methanol); analysis for $C_{10}H_{18}N_3O_7Cl$ (MW 327.72):

Calcd. (%) C, 36.65; H, 5.54; N, 12.82; Cl, 10.82. Found (%) C, 36.71; H, 5.52; N, 12.78; Cl, 10.67. While for the β-anomer: yield 33.0%; mp 121°–123° C. (decomp.); $[α]_D^{25} -6°$ (C 1.0, methanol); analysis for $C_{10}H_{18}N_3O_7Cl$ (MW 327.72):

Calcd. (%) C, 36.65; H, 5.54; N, 12.82; Cl, 10.82. Found (%) C, 36.61; H, 5.64; N, 12.95; Cl, 10.93.

The Kieselgel-60 chromatography column from which the α- and β-anomer fractions have been separated in the above is further treated with chloroform-ethanol (4:1), and the eluate therefrom is concentrated under reduced pressure. The crystalline residue obtained is recrystallized from methanol to give 0.5 g of methyl 6-amino-6-deoxy-α-D-glucopyranoside-4,6-carbamate. Yield 7.6%. mp 141°–143° C. $[α]_D^{25} +38.5°$ (C 0.5, water). Analysis for $C_8H_{13}NO_6$ (MW 219.20):

Calcd. (%) C, 43.84; H, 5.98; N, 6.39. Found (%) C, 44.01; H, 6.00; N, 6.29.

EXAMPLE 12

6.70 g (24.5 mmol) of o-nitrophenyl N-(2-chloroethyl)-N-nitrosocarbamate is dissolved in a mixture of 20 ml toluene and 20 ml ethylacetate, and to this solution is added dropwise a solution prepared by dissolving (partially suspending) 1.92 g (10 mmol) of methyl 2,6-di-amino-2,6-di-deoxy-α-D-glucopyranoside in 20 ml of methanol, while stirring, at 20°–22° C. over 15 minutes. The resultant mixture is stirred at the same temperature for a further 2 hours. The thus reacted solution is concentrated at 30° C. and below, under reduced pressure. The crystalline residue obtained is washed with methyl ethyl ketone, dried under reduced pressure, and recrystallized from anhydrous ethanol to give 3.78 g of 3,3'-(methyl α-D-glucopyranos-2,6-di-yl)-bis[1-(2-chloroethyl)-1-nitrosourea]. Yield 82.0%. mp 146°–147° C. (decomp.). $[α]_D^{25} +103°$ (C 0.3, methanol).

Analysis for $C_{13}H_{22}N_6O_8Cl_2$ (MW 461.26):

Calcd. (%) C,33.85; H,4.81; N,18.22; Cl,15.37. Found (%) C,33.91; H,4.84; N,18.17; Cl,15.32.

EXAMPLE 13

6.70 g (24.5 mmol) of o-nitrophenyl N-(2-chloroethyl)-N-nitrosocarbamate is dissolved in a mixture of 15 ml tetrahydrofuran and 15 ml acetonitrile, and to this solution is added dropwise a solution prepared by dissolving (partially suspending) 2.34 g (10 mmol) of n-butyl 2,6-di-amino-2,6-di-deoxy-β-D-glucopyranoside in 30 ml of isopropanol, while stirring, at 20°–22° C. over 10 minutes. The resultant mixture is stirred at the same temperature for a further 2.5 hours, and thus reacted solution is concentrated at 30° C. and below, under reduced pressure. The crystalline residue obtained is washed with ethyl ether, dried under reduced pressure, and recrystallized from anhydrous ethanol to give 3.87 g of 3,3'-(n-butyl β-D-glucopyranos-2,6-di-yl)-bis[1-(2-chloroethyl)-1-nitrosourea]. Yield 76.9%. mp 125°–127° C. (decomp.). $[α]_D^{25} -6.5°$ (C 0.5, water). Analysis for $C_{16}H_{28}N_6O_8Cl_2$ (MW 503.34):

Calcd. (%) C,38.18; H,5.61; N,16.70; Cl,14.09. Found (%) C,38.40; H,5.57; N,16.82; Cl,14.12.

EXAMPLE 14

Analogously to Example 12 using 6.20 g (24.5 mmol) of o-cyanophenyl N-(2-chloroethyl)-N-nitrosocarbamate in place of 6.70 g of o-nitrophenyl N-(2-chloroethyl)-N-nitrosocarbamate, there is obtained 3.77 g of 3,3'-(methyl α-D-glucopyranos-2,6-di-yl)-bis[1-(2-chloroethyl)-1-nitrosourea]. Yield 81.8%. mp 146°–147° C. (decomp.). $[α]_D^{25} +103°$ (C 0.3, methanol). Analysis for $C_{13}H_{22}N_6O_8Cl_2$ (MW 461.26):

Calcd. (%) C,33.85; H,4.81; N,18.22; Cl,15.37. Found (%) C,33.96; H,4.82; N,18.16; Cl,15.31.

EXAMPLE 15

6.70 g (24.5 mmol) of o-nitrophenyl N-(2-chloroethyl)-N-nitrosocarbamate is dissolved in 30 ml of dioxane, and to this solution is added dropwise a solution prepared by dissolving 1.78 g (10 mmol) of 2,6-di-amino-2,6-di-deoxy-D-glucopyranose in a mixture of 10 ml methanol and 10 ml dimethylformamide, while stirring, at 10°–20° C. over 20 minutes. The resultant mixture is stirred at the same temperature for a further 2.5 hours. The thus reacted solution is concentrated at 30° C. and below, under reduced pressure. The crystalline residue obtained is washed with ethyl acetate and then with ethyl ether, dried under reduced pressure, and recrystallized from anhydrous ethanol to give 3.72 g of 3,3'-(D-glucopyranos-2,6-di-yl)-bis[1-(2-chloroethyl)-1-nitrosourea]. Yield 83.2%. mp 125°–127° C. (decomp.). Analysis for $C_{12}H_{20}N_6O_8Cl_2$ (MW 447.23):

Calcd. (%) C,32.23; H,4.51; N,18.79; Cl,15.85. Found (%) C,32.17; H,4.48; N,18.73; Cl,15.82.

EXAMPLE 16

96.0 g (0.5 mol) of methyl 2,6-di-amino-2,6-di-deoxy-α-D-glucopyranoside is dissolved in 500 ml of methanol, and to this solution is added 140.8 g (3.2 mol) of dry-ice little by little so as to convert the glucopyranoside into its carbonic acid-addition salt. This acid-addition salt solution is then added dropwise to the solution, which has been prepared by dissolving 327.6 g (1.20 mol) of o-nitrophenyl N-(2-chloroethyl)-N-nitrosocarbamate in a mixture of 500 ml tetrahydrofuran and 500 ml dioxane and which has been cooled to 0°–5° C., while stirring, over an hour. The resultant mixture is stirred further at 22°–25° C. for 2 hours, and the thus reacted solution is concentrated at 40° C. and below, under reduced pressure. The crystalline residue obtained is washed with acetone, dried under reduced pressure, and recrystallized from anhydrous ethanol to give 200.6 g of 3,3'-(methyl α-D-glucopyranos-2,6-di-yl)-bis[1-(2-chloroethyl)-1-nitrosourea]. Yield 87.0%. mp 146°–147° C. (decomp.) $[α]_D^{25} +103°$ (C 0.3, methanol). Analysis for $C_{13}H_{22}N_6O_8Cl_2$ (MW 461.26):

Calcd. (%) C,33.85; H,4.81; N,18.22; Cl,15.37. Found (%) C,33.90; H,4.85; N,18.20; Cl,15.26.

EXAMPLE 17

1.79 g (10 mmol) of 2-amino-2-deoxy-D-glucopyranose is dissolved in a mixture of 10 ml methanol and 5 ml dimethyl sulfoxide, and this solution is added dropwise to a solution prepared by dissolving 3.28 g (12 mmol) of o-nitrophenyl N-(2-chloroethyl)-N-nitrosocarbamate in a mixture of 10 ml methylene chloride and 10 ml tetrahydrofuran, while stirring, at 20°–25° C. over 10 minutes. The resultant mixture is stirred at the same temperature for a further 1.5 hours. The thus reacted solution is concentrated at 40° C. and below, under reduced pressure. The crystalline residue obtained is washed with petroleum ether, dried under reduced pressure, and recrystallized from ethanol to give 2.56 g of 3-(D-glucopyranos-2-yl)-1-(2-chloroethyl)-1-nitrosourea. Yield 81.6%. mp 147°–148° C. (decomp.). Analysis for $C_9H_{16}N_3O_7Cl$ (MW 313.69):

Calcd. (%) C,34.46; H,5.14; N,13.40; Cl,11.30. Found (%) C,34.32; H,5.16; N,13.29; Cl,11.19.

EXAMPLE 18

3.28 g (12 mmol) of o-nitrophenyl N-(2-chloroethyl)-N-nitrosocarbamate is dissolved in a mixture of 20 ml dioxane and 10 ml ethylacetate, and to this solution is added dropwise a solution prepared by dissolving 1.93 g (10 mmol) of methyl 2-amino-2-deoxy-α-D-glucopyranoside in 15 ml of methanol, while stirring, at 20°–22° C. over 10 minutes. The resultant mixture is stirred at the same temperature for a further hour, and the thus reacted solution is concentrated at 40° C. and below, under reduced pressure. The crystalline residue obtained is washed with ethyl ether, dried under reduced pressure, and recrystallized from anhydrous ethanol to give 2.67 g of 3-(methyl α-D-glucopyranos-2-yl)-1-(2-chloroethyl)-1-nitrosourea. Yield 81.4%. mp 144°–146° C. (decomp.). $[\alpha]_D^{25}+104°$ (C 0.5, methanol).

Analysis for $C_{10}H_{18}N_3O_7Cl$ (MW 327.72): Calcd. (%) C,36.65; H,5.54; N,12.82; Cl,10.82. Found (%) C,36.72; H,5.64; N,12.78; Cl,10.86.

EXAMPLE 19

Analogously to Example 18 using methyl 2-amino-2-deoxy-β-D-glucopyranoside in place of methyl 2-amino-2-deoxy-α-D-glucopyranoside, there is obtained 2.65 g of 3-(methyl β-D-glucopyranos-2-yl)-1-(2-chloroethyl)-1-nitrosourea. Yield 80.8%. mp 152°–154° C. (decomp.). $[\alpha]_D^{25}-4.4°$ (C 0.5, methanol). Analysis for $C_{10}H_{18}N_3O_7Cl$ (MW 327.72):

Calcd. (%) C,36.65; H,5.54; N,12.82; Cl,10.82. Found (%) C,36.61; H,5.63; N,12.93; Cl,10.75.

EXAMPLE 20

3.04 g (12 mmol) of o-cyanophenyl N-(2-chloroethyl)-N-nitrosocarbamate is dissolved in a mixture of 10 ml carbon tetrachloride and 10 ml tetrahydrofuran, and to this solution is added dropwise a solution prepared by dissolving 1.93 g (10 mmol) of methyl 2-amino-2-deoxy-α-D-glucopyranoside in 15 ml of methanol, while stirring, at 30°–35° C. over 10 minutes. Thereafter, a similar procedure to that of Example 18 is carried out, to give 2.49 g of 3-(methyl α-D-glucopyranos-2-yl)-1-(2-chloroethyl)-1-nitrosourea. Yield 75.9%. mp 144°–146° C. (decomp.). $[\alpha]_D^{25}+104°$ (C 0.5, methanol). Analysis for $C_{10}H_{18}N_3O_7Cl$ (MW 327.72):

Calcd. (%) C,36.65; H,5.54; N,12.82; Cl,10.82. Found (%) C,36.61; H,5.63; N,12.91; Cl,10.74.

EXAMPLE 21

3.28 g (12 mmol) of o-nitrophenyl N-(2-chloroethyl)-N-nitrosocarbamate is dissolved in 30 ml of dioxane, and to this solution is added dropwise a solution prepared by dissolving (partially suspending) 2.35 g (10 mmol) of n-butyl 2-amino-2-deoxy-α-D-glucopyranoside in 30 ml of ethanol, while stirring, at 20°–25° C. over 15 minutes. The resultant mixture is stirred at the same temperature for a further hour, and the thus reacted solution is then concentrated at 40° C. and below, under reduced pressure. The crystalline residue obtained is washed with ethyl ether and then with acetone, dried under reduced pressure, and recrystallized from isopropanol to give 2.93 g of 3-(n-butyl α-D-glucopyranos-2-yl)-1-(2-chloroethyl)-1-nitrosourea as pale yellowish crystals. Yield 79.2%. mp 138°–140° C. (decomp.). $[\alpha]_D^{25}+118°$ (C 0.2, methanol).

Analysis for $C_{13}H_{24}N_3O_7Cl$ (MW 369.80): Calcd. (%) C,42.22; H,6.54; N,11.36; Cl,9.59. Found (%) C,42.28; H,6.62; N,11.38; Cl,9.52.

EXAMPLE 22

3.28 g (12 mmol) of o-nitrophenyl N-(2-chloroethyl)-N-nitrosocarbamate is dissolved in 20 ml of anhydrous tetrahydrofuran, and to this solution is added dropwise a solution prepared by dissolving 2.35 g (10 mmol) of n-butyl 2-amino-2-deoxy-β-D-glucopyranoside in 30 ml of anhydrous methanol, while stirring, at about 30° C. over 15 minutes. The resultant mixture is stirred at the same temperature for a further hour, and the thus reacted solution is concentrated at 50° C. and below, under reduced pressure. The crystalline residue obtained is washed with n-hexane and then with methyl ethyl ketone, dried under reduced pressure, and recrystallized from anhydrous ethanol to give 3.01 g of 3-(n-butyl β-D-glucopyranos-2-yl)-1-(2-chloroethyl)-1-nitrosourea. Yield 81.3%. mp 150°–152° C. (decomp.). $[\alpha]_D^{25}-30°$ (C 0.3, methanol). Analysis for $C_{13}H_{24}N_3O_7Cl$ (MW 369.80):

Calcd. (%) C,42.22; H,6.54; N,11.36; Cl,9.59. Found (%) C,42.28; H,6.60; N,11.32; Cl,9.52.

EXAMPLE 23

Analogously to Example 21 using 2.21 g (10 mmol) of n-propyl 2-amino-2-deoxy-α-D-glucopyranoside in place of 2.35 g of n-butyl 2-amino-2-deoxy-α-D-glucopyranoside, there is obtained 2.62 g of 3-(n-propyl α-D-glucopyranos-2-yl)-1-(2-chloroethyl)-1-nitrosourea as pale yellowish crystals. Yield 73.6%. mp 122°–124° C. (decomp.). $[\alpha]_D^{25}+86°$ (C 0.5, water). Analysis for $C_{12}H_{22}N_3O_7Cl$ (MW 355.77):

Calcd. (%) C,40.51; H,6.23; N,11.81; Cl,9.97. Found (%) C,40.45; H,6.38; N,11.92; Cl,10.04.

EXAMPLE 24

2.70 g (12 mmol) of o-nitrophenyl N-methyl-N-nitrosocarbamate is dissolved in 20 ml of toluene, and to this solution is added dropwise a solution prepared by dissolving (partially suspending) 1.93 g (10 mmol) of methyl 2-amino-2-deoxy-α-D-glucopyranoside in 30 ml of ethanol, while stirring, at about 50° C. over 15 minutes. The resultant mixture is stirred at the same temperature for a further 1.5 hours, and the thus reacted solution is concentrated at 50° C. and below, under reduced pressure. The crystalline residue obtained is washed with n-hexane and then with acetone, dried under reduced pressure, and recrystallized from ethanol to give 2.13 g of 3-(methyl α-D-glucopyranos-2-yl)-1-methyl-1-nitrosourea. Yield 76.3%. mp 130°-133° C. (decomp.). $[\alpha]_D^{25}+107°$ (C 0.5, water). Analysis for $C_9H_{17}N_3O_7$ (MW 279.25):

Calcd. (%) C,38.71; H,6.14; N,15.05. Found (%) C,39.02; H,6.31; N,14.90.

Analogously to the above using methyl 2-amino-2-deoxy-β-D-glucopyranoside in place of methyl 2-amino-2-deoxy-α-D-glucopyranoside, there is obtained 2.08 g of 3-(methyl β-D-glucopyranos-2-yl)-1-methyl-1-nitrosourea. Yield 74.5%. mp 185°-187° C. (decomp.). $[\alpha]_D^{25}-21.0°$ (C 0.5, water). Analysis for $C_9H_{17}N_3O_7$ (MW 279.25):

Calcd. (%) C,38.71; H,6.14; N,15.05. Found (%) C,38.89; H,6.21; N,14.86.

EXAMPLES 25-32

Analogously to Example 24, in each case using other nitrosocarbamate compounds (12.0 mmol each) and glucopyranoside compounds (10.0 mmol each) instead of o-nitrophenyl N-methyl-N-nitrosocarbamate and methyl 2-amino-2-deoxy-α(or β)-D-glucopyranoside respectively, there are obtained other glucopyranose-nitrosourea compounds. The results are shown in Table VII.

tained is washed with anhydrous ethyl ether and then with acetone, dried under reduced pressure, and recrystallized from anhydrous ethanol to give 143.0 g of 3-(methyl α-D-glucopyranos-2-yl)-1-(2-chloroethyl)-1-nitrosourea. Yield 87.3%. mp 144°-146° C. (decomp.). $[\alpha]_D^{25}+104°$ (C 0.5, methanol). Analysis for $C_{10}H_{18}N_3O_7Cl$ (MW 327.72):

Calcd. (%) C,36.65; H,5.54; N, 12.82; Cl,10.82. Found (%) C,36.73; H,5.68; N,12.67; Cl,10.75.

EXAMPLE 34

3.28 g (12 mmol) of o-nitrophenyl N-(2-chloroethyl)-N-nitrosocarbamate is dissolved in a mixture of 10 ml anhydrous dimethylformamide and 10 ml anhydrous ethanol, and to this solution is added little by little 1.79 g (10 mmol) of 1-amino-1-deoxy-β-D-glucopyranose powder, while stirring, at 5°-10° C. over 10 minutes. The resultant mixture is, after adding 5 ml of anhydrous dimethylformamide thereto, stirred further at 10° C. for 5 hours, and the thus reacted solution is concentrated at 40° C. and below, under reduced pressure. The crystalline residue obtained is washed with anhydrous ethyl ether and then with acetone, dried under reduced pressure, and recrystallized from anhydrous ethanol-ethyl ether (1:5) to give 2.47 g of 3-(β-D-glucopyranosyl)-1-(2-chloroethyl)-1-nitrosourea. Yield 78.7%. mp 77°-78° C. (decomp.). $[\alpha]_D^{25}-10.3°$ (C 1.0, water). Analysis for Table VII

| Example No. | Nitrosocarbamate compound | Glucopyranoside compound | Glucopyranose-nitrosourea compound | | |
|---|---|---|---|---|---|
| | | | Chemical name | Yield % | mp, °C. (decomp.) | $[\alpha]_D^{25}$ C 0.5, water |
| 25 | o-nitrophenyl N-n-propyl-N-nitrosocarbamate | methyl 2-amino-2-deoxy-α-D-glucopyranoside | 3-(methyl α-D-glucopyranos-2-yl)-1-n-propyl-1-nitrosourea | 77.0 | 118-120 | +88 |
| 26 | o-nitrophenyl-N-ethyl-N-nitrosocarbamate | ethyl 2-amino-2-deoxy-α-D-glucopyranoside | 3-(ethyl α-D-glucopyranos-2-yl)-1-ethyl-1-nitrosourea | 72.4 | 114-116 | +135° |
| 27 | o-cyanophenyl N-ethyl-N-nitrosocarbamate | ethyl 2-amino-2-deooxy-β-D-glucopyranoside | 3-(ethyl β-D-glucopyranos-2-yl)-1-ethyl-1-nitrosourea | 70.2 | 122-124 | -26° |
| 28 | o-nitrophenyl N-methyl-N-nitrosocarbamate | n-propyl 2-amino-2-deoxy-α-D-glucopyranoside | 3-(n-propyl α-D-glucopyranos-2-yl)-1-methyl-1-nitrosourea | 73.5 | 112-114 | +142° |
| 29 | o-nitrophenyl N-methyl-N-nitrosocarbamate | n-butyl 2-amino-2-deoxy-β-D-glucopyranoside | 3-(n-butyl β-D-glucopyranos-2-yl)-1-methyl-1-nitrosourea | 78.8 | 214-216 | -45° |
| 30 | o-nitrophenyl N-methyl-N-nitrosocarbamate | methyl 6-amino-6-deoxy-α-D-glucopyranoside | 3-(methyl α-D-glucopyranos-6-yl)-1-methyl-1-nitrosourea | 80.2 | 143-146 | +102° |
| 31 | o-cyanophenyl N-ethyl-N-nitrosocarbamate | ethyl 6-amino-6-deoxy-β-D-glucopyranoside | 3-(ethyl β-D-glucopyranos-6-yl)-1-ethyl-1-nitrosourea | 72.3 | 136-138 | -20° |
| 32 | o-nitrophenyl N-n-butyl-N-nitrosocarbamate | n-propyl 6-amino-6-deoxy-α-D-glucopyranoside | 3-(n-propyl α-D-glucopyranos-6-yl)-1-n-butyl-1-nitrosourea | 74.2 | 112-114 | +122° |

EXAMPLE 33

96.6 g (0.50 mol) of methyl 2-amino-2-deoxy-α-D-glucopyranoside is dissolved in 500 ml of anhydrous methanol, and the solution is cooled to 0°-5° C. To this solution is added 66.0 g (1.5 mol) of dry-ice little by little so as to convert the glucopyranoside into its carbonic acid-addition salt. This acid-addition salt solution is then added dropwise to a solution prepared by dissolving 163.8 g (0.60 mol) of o-nitrophenyl N-(2-chloroethyl)-N-nitrosocarbamate in a mixture of 500 ml anhydrous tetrahydrofuran and 500 ml toluene, while stirring, at 0°-5° C. over an hour. The resultant mixture is stirred further at 22°-25° C. for 2 hours. The thus reacted solution is concentrated at 50° C. and below, under reduced pressure. The crystalline residue ob-

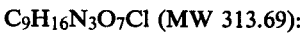

$C_9H_{16}N_3O_7Cl$ (MW 313.69):

Calcd. (%) C,34.46; H,5.14; N,13.40; Cl,11.30. Found (%) C,34.41; H,5.18; N,13.52; Cl,11.42.

EXAMPLE 35

Analogously to Example 34 using 3.04 g (12 mmol) of o-cyanophenyl N-(2-chloroethyl)-N-nitrosocarbamate in place of 3.28 g of o-nitrophenyl N-(2-chloroethyl)-N-nitrosocarbamate, there is obtained 2.33 g of 3-(β-D-glucopyranosyl)-1-(2-chloroethyl)-1-nitrosourea. Yield 74.3%. mp 77°-78° C. (decomp.). $[\alpha]_D^{25}-10.3°$ (C 1.0, water).

EXAMPLE 36

1.79 g (10 mmol) of 1-amino-1-deoxy-$\beta$-D-glucopyranose is dissolved (partially suspended) in 40 ml of anhydrous ethanol, and the solution is cooled to 0°–5° C. To this solution is added 2.2 g (50 mmol) of dry-ice little by little so as to convert the glucopyranose into its carbonic acid-addition salt. This acid-addition salt solution is then added dropwise to a solution prepared by dissolving 3.28 g (12 mmol) of o-nitrophenyl N-(2-chloroethyl)-N-nitrosocarbamate in a mixture of 40 ml anhydrous tetrahydrofuran and 10 ml benzene, while stirring, at 0°–5° C. over an hour. The resultant mixture is stirred further at 20°–25° C. for 2 hours, and the thus reacted solution is concentrated at 50° C. and below, under reduced pressure. The crystalline residue obtained is washed with anhydrous ethyl ether and then with acetone, dried under reduced pressure, and recrystallized from anhydrous isopropanol to give 2.72 g of 3-($\beta$-D-glucopyranosyl)-1-(2-chloroethyl)-1-nitrosourea. Yield 86.8%. mp 77°–78° C. (decomp.). $[\alpha]_D^{25} -10.3°$ (C 1.0, water). Analysis for $C_9H_{16}N_3O_7Cl$ (MW 313.69):

Calcd. (%) C,34.46; H,5.14; N,13.40; Cl,11.30. Found (%) C,34.52; H,5.10; N,13.32; Cl,11.26.

EXAMPLE 37

Analogously to Example 36 using 3.04 g (12 mmol) of o-cyanophenyl N-(2-chloroethyl)-N-nitrosocarbamate in place of 3.28 g of o-nitrophenyl N-(2-chloroethyl)-N-nitrosocarbamate, there is obtained 2.68 g of 3-($\beta$-D-glucopyranosyl)-1-(2-chloroethyl)-1-nitrosourea. Yield 85.3%. mp 77°–78° C. (decomp.). $[\alpha]_D^{25} -11°$ (C 1.0, water).

EXAMPLE 38

Analogously to Example 36 using 2-amino-2-deoxy-D-glucopyranose in place of 1-amino-1-deoxy-$\beta$-D-glucopyranose, there is obtained 2.71 g of 3-(D-glucopyranos-2-yl)-1-(2-chloroethyl)-1-nitrosourea. Yield 86.5%. mp 147°–148° C. (decomp.). Analysis for $C_9H_{16}N_3O_7Cl$ (MW 313.69):

Calcd. (%) C,34.46; H,5.14; N,13.40; Cl,11.30. Found (%) C,34.52; H,5.19; N,13.37; Cl,11.41.

EXAMPLE 39

1.79 g (10 mmol) of 2-amino-2-deoxy-D-glucopyranose is dissolved in a mixture of 20 ml anhydrous methanol and 10 ml dimethylformamide, and the solution is cooled to 0°–5° C. To this solution is added 2.2 g (50 mmol) of dry-ice little by little so as to convert said glucopyranose into its carbonic acid-addition salt. This acid-addition salt solution is then added dropwise to a solution prepared by dissolving 3.04 g (12 mmol) of o-cyanophenyl N-(2-chloroethyl)-N-nitrosocarbamate in a mixture of 20 ml anhydrous tetrahydrofuran and 10 ml methylene chloride, while stirring, at 0°–5° C. over an hour. The resultant mixture is stirred further at 22°–25° C. for 2 hours, and the thus reacted solution is concentrated at 40° C. and below, under reduced pressure. The crystalline residue obtained is washed with petroleum ether, dried under reduced pressure, and recrystallized from anhydrous ethanol to give 2.58 g of 3-(D-glucopyranos-2-yl)-1-(2-chloroethyl)-1-nitrosourea. Yield 82.2%. mp 147°–148° C. (decomp.). Analysis for $C_9H_{16}N_3O_7Cl$ (MW 313.69):

Calcd. (%) C,34.46; H,5.14; N,13.40; Cl,11.30. Found (%) C,34.54; H,5.08; N,13.32; Cl,11.23.

EXAMPLE 40

1.79 g (10 mmol) of 6-amino-6-deoxy-D-glucopyranose is dissolved in a mixture of 20 ml anhydrous ethanol and 20 ml dimethyl sulfoxide, and the solution is cooled to 0°–5° C. To this solution is added 3.3 g (75 mmol) of dry-ice little by little so as to convert the glucopyranose into its carbonic acid-addition salt. This acid-addition salt solution is then added dropwise to a solution prepared by dissolving 3.28 g (12 mmol) of o-nitrophenyl N-(2-chloroethyl)N-nitrosocarbamate in a mixture of 40 ml anhydrous tetrahydrofuran and 10 ml toluene, while stirring, at 0°–5° C. over 30 minutes. The resultant mixture is stirred further at 20°–25° C. for 2 hours, and the thus reacted solution is concentrated at 40° C. and below, under reduced pressure. To the oily residue thus produced is added 80 ml of ethyl ether and the solution is left at 4° C. overnight. The crystalline residue obtained is washed with chloroform and then with ethyl ether, dried under reduced pressure, and recrystallized from anhydrous ethanol-n-hexane (4:1) to give 2.70 g of 3-(D-glucopyranos-6-yl)-1-(2-chloroethyl)-1-nitrosourea. Yield 86.1%. mp 102°–103° C. (decomp.). $[\alpha]_D^{20} +55°$ (C 0.5, methanol; the value of +55° reduced to +37° after 18 hours). Analysis for $C_9H_{16}N_3O_7Cl$ (MW 313.69):

Calcd. (%) C,34.46; H,5.14; N,13.40; Cl,11.30. Found (%) C,34.55; H,5.10; N,13.33; Cl,11.42.

By the way, 0.40 g (1.28 mmol) of 3-(D-glucopyranos-6-yl)-1-(2-chloroethyl)-1-nitrosourea obtained as above is added to a mixture of 7 ml pyridine and 5 ml acetic anhydride at 0°–5° C., and the mixture is stirred for 2 hours. Completion of the acetylating reaction is checked by thin-layer chromatography [silicagel; developing solvent:benzene-ethanol (5:1)], and the solution is then poured into about 1 liter of ice-water, with stirring. The crystalline residue produced is recrystallized from ethanol to give 0.16 g of 1-(2-chloroethyl)-1-nitroso-3-(tetra-O-acetyl-D-glucopyranos-6-yl)urea, said urea compound being a mixture of about 70% $\alpha$-anomer and about 30% $\beta$-anomer. Yield 26.1%. mp 115°–117° C. (decomp.). $[\alpha]_D^{23} +74°$ (C 0.5, methanol). Analysis for $C_{17}H_{24}N_3O_{11}Cl$ (MW 481.84):

Calcd. (%) C,42.38; H,5.02; N,8.72; Cl,7.36. Found: (%) C,42.49; H,5.13; N,8.68; Cl,7.44.

IR Spectrum (KBr,cm$^{-1}$):3375($\nu$N-H),1740($\nu$COCH$_3$),1715($\nu$C=O),1535($\delta$N-H),1485($\nu$N=O),1230($\nu$COCH$_3$).

NMR Spectrum (CDCl$_3$,$\delta$):2.05,2.14,2.20(12H,COCH$_3$),3.70(2H,triplet,CH$_2$CH$_2$Cl),4.18(2H,triplet,CH$_2$CH$_2$Cl),5.75(0.3H,doublet,J=7Hz,$\beta$-anomer's C$_1$-H),6.45(0.7H,doublet,J=4Hz,$\alpha$-anomer's C$_1$-H),7.20(1H,triplet,NH).

EXAMPLE 41

Analogously to the first preparation described in Example 40 using 3.17 g (12.5 mmol) of o-cyanophenyl N-(2-chloroethyl)-N-nitrosocarbamate in place of 3.28 g of o-nitrophenyl N-(2-chloroethyl)-N-nitrosocarbamate, there is obtained 2.66 g of 3-(D-glucopyranos-6-yl)-1-(2-chloroethyl)-1-nitrosourea. Yield 84.8%. mp 102°–103° C. (decomp.). $[\alpha]_D^{20} +55°$ (C 0.5, methanol; the value of +55° reduced to +31° after 22 hours). Analysis for $C_9H_{16}N_3O_7Cl$ (MW 313.69):

Calcd. (%) C,34.46; H,5.14; N,13.40; Cl,11.30. Found (%) C,34.52; H,5.08; N,13.45; Cl,11.45.

EXAMPLE 42

Analogously to Example 16 using 117.0 g (0.50 mol) of n-butyl 2,6-di-amino-2,6-di-deoxy-β-D-glucopyranoside in place of 96.0 g of methyl 2,6-di-amino-2,6-di-deoxy-α-D-glucopyranoside, there is obtained 214.4 g of 3,3'-(n-butyl β-D-glucopyranos-2,6-di-yl)-bis[1-(2-chloroethyl)-1-nitrosourea]. Yield 85.2%. mp 125°–127° C. (decomp.). $[\alpha]_D^{25} -7°$ (C 0.5, water). Analysis for $C_{16}H_{28}N_6O_8Cl_2$ (MW 503.34):

Calcd (%) C,38.18; H,5.61; N,16.70; Cl,14.09. Found (%) C,38.29; H,5.75; N,16.52; Cl,14.22.

EXAMPLE 43

9.66 g (50 mmol) of methyl 2-amino-2-deoxy-α-D-glucopyranoside is dissolved in a mixture of 100 ml methanol and 20 ml dimethyl sulfoxide, and to this solution is added citric acid powder, with stirring, to adjust the pH of the solution to 9.5. The resulting solution is then added dropwise to a solution prepared by dissolving 16.4 g (60 mmol) of o-nitrophenyl N-(2-chloroethyl)-N-nitrosocarbamate in a mixture of 150 ml tetrahydrofuran and 100 ml toluene, while stirring, at 0°–5° C. over 10 minutes. The resultant mixture is stirred further at 20°–25° C. for 2 hours, and the thus reacted solution is concentrated at 40° C. and below, under reduced pressure. The crystalline residue obtained is washed with ethyl ether and then with acetone, dried under reduced pressure, and recrystallized from methanol to give 13.8 g of 3-(methyl α-D-glucopyranos-2-yl)-1-(2-chloroethyl)-1-nitrosourea. Yield 84.3%. mp 144°–146° C. (decomp.). $[\alpha]_D^{25} +104°$ (C 0.5, methanol). Analysis for $C_{10}H_{18}N_3O_7Cl$ (MW 327.72):

Calcd. (%) C,36.65; H,5.54; N,12.82; Cl,10.82. Found (%) C,36.57; H,5.58; N,12.89; Cl,10.76.

EXAMPLE 44

3.86 g (20 mmol) of methyl 6-amino-6-deoxy-α-D-glucopyranoside is dissolved in 40 ml of methanol, and to this solution is added formic acid dropwise, with stirring, to adjust the PH of the solution to 8.5. The resulting solution is then added dropwise to a solution prepared by dissolving 6.55 g (23.9 mmol) of o-nitrophenyl N-(2-chloroethyl)-N-nitrosocarbamate in a mixture of 30 ml tetrahydrofuran and 20 ml dioxane, while stirring, at 20°–24° C. over 20 minutes. The resultant mixture is stirred at the same temperature for a further 2 hours, and the thus reacted solution is concentrated at 30° C. and below, under reduced pressure. The crystalline residue obtained is washed with ethyl ether, dried under reduced pressure, and recrystallized from anhydrous ethanol-n-hexane (4:1) to give 5.43 g of 3-(methyl-α-D-glucopyranos-6-yl)-1-(2-chloroethyl)-1-nitrosourea. Yield 83.0%. mp 111°–113° C. (decomp.). $[\alpha]_D^{25} +94°$ (C 0.5, methanol).

Analysis for $C_{10}H_{18}N_3O_7Cl$ (MW 327.72): Calcd. (%) C,36.65; H,5.54; N,12.82; Cl,10.82. Found (%) C,36.78; H,5.42; N,12.77; Cl,10.91.

EXAMPLE 45

2.35 g (10 mmol) of n-butyl 6-amino-6-deoxy-α-D-glucopyranoside is dissolved in a mixture of 50 ml isopropanol and 50 ml dimethylformamide, and to this solution is added succinic acid powder, with stirring, to adjust the PH of the solution to 9.1. The resulting solution is then added dropwise to a solution prepared by dissolving 3.17 g (12.5 mmol) of o-cyanophenyl N-(2-chloroethyl)-N-nitrosocarbamate in a mixture of 20 ml tetrahydrofuran and 10 ml benzene, while stirring, at 0°–10° C. over 30 minutes. The resultant mixture is stirred at the same temperature for a further 2 hours, and thus reacted solution is, after filtering, concentrated at 40° C. and below, under reduced pressure. The crystalline residue obtained is washed with n-hexane and then with ethyl ether, dried under reduced pressure, and recrystallized from isopropanol to give 3.13 g of 3-(n-butyl α-D-glucopyranos-6-yl)-1-(2-chloroethyl)-1-nitrosourea. Yield 84.6%. mp 108°–109° C. (decomp.). $[\alpha]_D^{25} +147°$ (C 0.5, water). Analysis for $C_{13}H_{24}N_3O_7Cl$ (MW 369.80):

Calcd. (%) C,42.22; H,6.54; N,11.36; Cl,9.59. Found (%) C,42.28; H,6.42; N,11.43; Cl,9.54.

EXAMPLE 46

1.79 g (10 mmol) of 6-amino-6-deoxy-D-glucopyranose is dissolved in a mixture of 10 ml methanol and 10 ml isopropanol, and to this solution is added formic acid dropwise, with stirring, to adjust the PH of the solution to 7.8. The resulting solution is then added dropwise to a solution prepared by dissolving 3.28 g (12 mmol) of o-nitrophenyl N-(2-chloroethyl)-N-nitrosocarbamate in a mixture of 10 ml tetrahydrofuran and 10 ml ethylacetate, while stirring, at 0°–5° C. over 30 minutes. The resultant mixture is stirred at the same temperature for a further 2 hours, and the thus reacted solution is concentrated at 30° C. and below, under reduced pressure. To the oily residue produced is added ethyl ether and the solution is left at 0°–5° C. overnight. The crystalline residue obtained is washed with chloroform and further with ethyl ether, dried under reduced pressure, and recrystallized from anhydrous ethanol-n-hexane (4:1) to give 2.71 g of 3-(D-glucopyranos-6-yl)-1-(2-chloroethyl)-1-nitrosourea. Yield 86.3%. mp 102°–103° C. (decomp.). $[\alpha]_D^{20} +55°$ (C 0.5, methanol; the value of +55° reduced to +31° after 22 hours).

Analysis for $C_9H_{16}N_3O_7Cl$ (MW 313.69): Calcd. (%) C,34.46; H,5.14; N,13.40; Cl,11.30. Found (%) C,34.38; H,5.13; N,13.32; Cl,11.45.

EXAMPLE 47

Analogously to Example 46 using 2-amino-2-deoxy-D-glucopyranose in place of 6-amino-6-deoxy-D-glucopyranose, there is obtained 2.58 g of 3-(D-glucopyranos-2-yl)-1-(2-chloroethyl)-1-nitrosourea. Yield 82.3%. mp 147°–148° C. (decomp.). Analysis for $C_9H_{16}N_3O_7Cl$ (MW 313.69):

Calcd. (%) C,34.46; H,5.14; N,13.40; Cl,11.30. Found (%) C,34.42; H,5.07; N,13.52; Cl,11.21.

EXAMPLE 48

2.20 g (10 mmol) of n-propyl 2,6-di-amino-2,6-di-deoxy-α-D-glucopyranoside is dissolved in a mixture of 10 ml isopropanol and 5 ml dimethyl sulfoxide, and to this solution is added lactic acid dropwise, with stirring, to adjust the PH of the solution to 8.3. The resulting solution is then added dropwise to a solution prepared by dissolving 6.10 g (24 mmol) of o-cyanophenyl N-(2-chloroethyl)-N-nitrosocarbamate in a mixture of 20 ml tetrahydrofuran and 10 ml isopropanol, while stirring, at 0°–5° C. over 30 minutes. The resultant mixture is stirred further at 22°–25° C. for 2 hours, and the thus reacted solution is concentrated at 30° C. and below, under reduced pressure. The crystalline residue obtained is washed with n-hexane and then with ethyl ether, dried under reduced pressure, and recrystallized from anhydrous ethanol-n-hexane (4:1) to give 4.08 g of 3,3'-(n-propyl α-D-glucopyranos-2,6-di-yl)-bis[1-(2-chloroethyl)-1-nitrosourea]. Yield 83.4%. mp 117°-119° C. (decomp.). $[\alpha]_D^{25}$ +110° (C 0.5, methanol). Analysis for $C_{15}H_{26}N_6O_8Cl_2$ (MW 489.31):

Calcd. (%) C,36.82; H,5.36; N,17.18; Cl,14.49. Found (%) C,36.73; H,5.42; N,17.29; Cl,14.35.

EXAMPLE 49

1.79 g (10 mmol) of 1-amino-1-deoxy-β-D-glucopyranose is dissolved in a mixture of 20 ml methanol and 10 ml dioxane, and to this solution is added a mixture of formic acid and citric acid dropwise, with stirring, to adjust the PH of the solution to 9.1. The resulting solution is then added dropwise to a solution prepared by dissolving 3.28 g (12 mmol) of o-nitrophenyl N-(2-chloroethyl)-N-nitrosocarbamate in a mixture of 10 ml tetrahydrofuran and 15 ml dioxane, while stirring, at 5°-10° C. over 30 minutes. The resultant mixture is stirred at the same temperature for a further 4 hours, and the thus reacted solution is concentrated at 40° C. and below, under reduced pressure. The crystalline residue obtained is washed with anhydrous ethyl ether and then with acetone, dried under reduced pressure, and recrystallized from anhydrous ethanol-ethyl ether (4:1) to give 2.56 g of 3-(β-D-glucopyranosyl)-1-(2-chloroethyl)-1-nitrosourea. Yield 81.5%. mp 77°-78° C. (decomp.). $[\alpha]_D^{25}$ −10.3° (C 1.0, water). Analysis for $C_9H_{16}N_3O_7Cl$ (MW 313.69):

Calcd. (%) C,34.46; H,5.14; N,13.40; Cl,11.30. Found (%) C,34.42; H,5.08; N,13.29; Cl,11.42.

What I claim is:

1. Process for the production of glucopyranosenitrosourea compounds having the general formula:

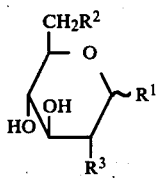

which comprises reacting an amino-glucopyranose compound having the general formula:

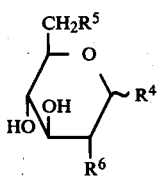

with a substituted-phenyl N-substituted-N-nitrosocarbamate compound having the general formula

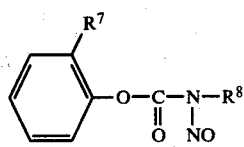

(in which $R^7$ represents a nitro or cyano group and $R^8$ is as hereinbefore defined).

2. Process as claimed in claim 1, wherein a compound of formula IV is used in which $R^4$ is hydroxy or alkoxy having from 1 to 4 carbon atoms; $R^5$ is amino or an acid addition salt formed therefrom; and $R^6$ is hydroxy.

3. Process as claimed in claim 1, wherein a compound of formula IV is used in which $R^4$ is hydroxy or alkoxy having from 1 to 4 carbon atoms; and each of $R^5$ and $R^6$ is amino or an acid-addition salt formed therefrom.

4. Process as claimed in claim 1 wherein a compound of formula IV is used in which $R^4$ is hydroxy or alkoxy having from 1 to 4 carbon atoms; $R^5$ is hydroxy; and $R^6$ is amino or an acid-addition salt formed therefrom.

5. Process as claimed in claim 1, wherein a compound of formula IV is used in which $R_4$ is amino or an acid addition salt formed therefrom; and each of $R^5$ and $R^6$ is hydroxy.

6. Process as claimed in claim 1, wherein $R^4$ in the compound of formula IV is one member selected from the group consisting of methoxy, ethoxy, n=propoxy and n-butoxy.

7. Process as claimed in claim 1, wherein at least one acid-addition salt is formed from weak acids.

8. Process as claimed in claim 7, wherein the weak acid is carbonic acid.

9. Process as claimed in claim 6, wherein a compound of formula V is used in which $R^7$ is a nitro group.

10. Process as claimed in claim 7, wherein a compound of formula V is used in which $R^7$ is a nitro group.

11. Process as claimed in claim 6, wherein a compound of formula V is used in which $R^7$ is a cyano group.

12. Process as claimed in claim 7, wherein a compound of formula V is used in which $R^7$ is a cyano group.

13. Process as claimed in claim 10, wherein the reaction is effected at a temperature of not more than 60° C.

14. Process as claimed in claim 3, wherein the reaction is effected at a temperature of not more than 60° C.

15. Process as claimed in claim 4, wherein the reaction is effected at a temperature of not more than 80° C.

16. Process as claimed in claim 5, wherein the reaction is effected at a temperature of not more than 30° C.

17. Process as claimed in claim 13, wherein the reaction is effected in the presence of a mixture of one member selected from the group consisting of methanol, ethanol and isopropanol with one member selected from the group consisting of tetrahydrofuran, toluene, dioxane, benzene, ethylacetate, isopropyl ether, dimethylformamide and dimethyl sulfoxide.

18. Process as claimed in claim 14, wherein the reaction is effected in the presence of a mixture of one member selected from the group consisting of methanol, ethanol and isopropanol with one member selected from the group consisting of tetrahydrofuran, toluene, dioxane, ethylacetate, acetonitrile, dimethylformamide and dimethyl sulfoxide.

19. Process as claimed in claim 15, wherein the reaction is effected in the presence of a mixture of one member selected from the group consisting of methanol, ethanol and isopropanol with one member selected from the group consisting of tetrahydrofuran, toluene, dioxane, benzene, ethylacetate, methylene chloride, carbon tetrachloride, dimethylformamide and dimethyl sulfoxide.

20. Process as claimed in claim 16, wherein the reaction is effected in the presence of a mixture of one member selected from the group consisting of methanol, ethanol and isopropanol with one member selected from the group consisting of tetrahydrofuran, dioxane, benzene, ethylacetate, and dimethylformamide.

21. 1-(Alkyl or 2-chloroethyl)-3-(D-glucopyranos-6-yl)-1-nitrosourea compounds having the general formula:
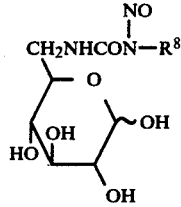
[II]
in which $R^8$ represents an alkyl group having from 1 to 4 carbon atoms or a 2-chloroethyl group.
22. Compounds as claimed in claim 21, wherein $R^8$ is any member selected from the group consisting of ethyl, methyl, n-propyl and n-butyl.
* * * * *